(12) United States Patent
Piccariello et al.

(10) Patent No.: US 8,716,300 B2
(45) Date of Patent: *May 6, 2014

(54) FREQUENCY MODULATED DRUG DELIVERY (FMDD)

(75) Inventors: Thomas Piccariello, Blacksburg, VA (US); Scott B. Palmer, Wilmette, IL (US); John D. Price, Blacksburg, VA (US); Robert Oberlender, Blacksburg, VA (US); Mary C. Spencer, Blacksburg, VA (US); Michaela E. Mulhare, Christiansburg, VA (US)

(73) Assignee: Synthonics, Inc., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/542,301

(22) Filed: Jul. 5, 2012

(65) Prior Publication Data

US 2012/0277256 A1    Nov. 1, 2012

Related U.S. Application Data

(63) Continuation of application No. 12/316,259, filed on Dec. 9, 2008, now Pat. No. 8,236,787.

(51) Int. Cl.
*A61K 31/522* (2006.01)
*C07D 233/00* (2006.01)
*C07D 473/00* (2006.01)

(52) U.S. Cl.
USPC ........ 514/263.3; 514/400; 514/626; 544/264; 548/338.1; 564/194

(58) Field of Classification Search
USPC ..................... 514/263.3, 400, 626; 544/265; 548/338.1; 564/194
See application file for complete search history.

(56) References Cited

U.S. PATENT DOCUMENTS

| | | | |
|---|---|---|---|
| 5,238,931 A | 8/1993 | Yoshikawa et al. |
| 5,373,093 A | 12/1994 | Vallarino et al. |
| 6,071,545 A | 6/2000 | Hendler et al. |
| 2002/0017305 A1 | 2/2002 | Bagrov et al. |
| 2002/0120165 A1 | 8/2002 | Zaworotko et al. |
| 2003/0224006 A1 | 12/2003 | Zaworotko et al. |
| 2004/0235712 A1 | 11/2004 | Lippard et al. |
| 2007/0026078 A1 | 2/2007 | Almarsson et al. |
| 2007/0059356 A1 | 3/2007 | Almarsson et al. |
| 2009/0209046 A1 | 8/2009 | Moulton et al. |
| 2009/0227446 A1 | 9/2009 | Chang et al. |
| 2010/0209354 A1 | 8/2010 | Horcajada-Cortes et al. |
| 2010/0226991 A1 | 9/2010 | Horcajada-Cortes et al. |
| 2010/0273642 A1 | 10/2010 | Chang et al. |
| 2010/0311701 A1 | 12/2010 | Almarsson et al. |
| 2011/0052650 A1 | 3/2011 | Morris et al. |

FOREIGN PATENT DOCUMENTS

EP    0914826 A1    5/1999
WO    WO 03/074474 A2    9/2003

OTHER PUBLICATIONS

Ama et al., Bull. Chem. Soc. Jpn., vol. 62, pp. 3464-3468 (1989).
International Preliminary Report on Patentability for International Application No. PCT/US2009/067136, issued Jun. 14, 2011 (6 pages).
International Search Report for International Application No. PCT/US2009/067136, mailed Mar. 16, 2010 (2 pages).
Islam, M. Saidul et al., "Antibacterial and antifungal activity of mixed ligand complexes of oxovanadium (IV), titanium (III) and cadmium (II) metal ions," Oriental Journal of Chemistry, 19(3):547-554 (2003).
Jain, Sangeeta, et al., "Synthesis and biological evaluation of mixed-ligand complexes of pyrazinamide and isoniazid," Oriental Journal of Chemistry, 20(2):409-410 (2004).
Khan, F, "Study of mixed ligand complexes of Zn<II> with some antibiotics and vitamin-B1 drugs, Kinetics of electrode reactions," Journal of the Indian Chemical Society, 84(7):702-705 (Jul. 2007).
Khan, Farid, et al., "Study of thermodynamics in the mixed ligand complexes of Zn(II) with antibiotics and ampicillin," Chemical & Environmental Research, 10(1&2):37-40 (2001).
Krymchantowski, A.V., et al., "The Future of Acute Care and Prevention in Heachache," Neurol. Sci., 2007, 28 Suppl 2, S166-S178.
Lenz et al., Biochemistry, vol. 3, No. 6, pp. 750-753 (1964).
Pool, J.L., "Direct Renin Inhibition: Focus on Aliskiren," J. Manag. Care Pharm., 2007, 13, S21-S33.
Siddiqui A et al., "Study of particle size and efficacy of transition metal complexes of mixed ligands, tolubutamide and gliclazide, the oral antidiabetic drugs," Biosciences Biotechnology Research Asia, 3(1):71-72 (Jun. 2005).
Singh, Rajender et al., "Solid, Solution, and antitumor activity studies of mixed-ligand complexes with adenine-5-bromouracil base pair," Synthesis and Reactivity in Inorganic and Metal-Organic Chemistry, 32(5):853-872 (2002).
Supplementary European Search Report for European Application No. 09836708.9, dated Aug. 17, 2012 (8 pages).
"Tekturna (aliskiren) Tablets 150mg-300mg," MedScape from WebMD, http://www.medscape.com/infosite/tekturna/article-pharmacology, 3 pgs. (2008).

(Continued)

*Primary Examiner* — Porfirio Nazario Gonzalez
(74) *Attorney, Agent, or Firm* — Brinks Gilson & Lione; Ryan L. Marshall

(57) ABSTRACT

Embodiments of the present disclosure include a coordination complex, comprising a first biologically active moiety, a second biologically active moiety, and a metal, wherein the first biologically active moiety and second biologically active moiety are bound to the metal by covalent coordination bonds, and wherein the first biologically active moiety and second biologically active moiety are different. These complexes may enhance the pharmacodynamic properties of biologically active moieties.

15 Claims, 10 Drawing Sheets

(56) References Cited

OTHER PUBLICATIONS

Thompson, Katherine H., et al., "Metal complexes in medicinal chemistry: new vistas and challenges in drug design," Dalton Transactions (Cambridge, England; 2003), 6:761-764 (Feb. 14, 2006).
Acharya, M.R.; Sparreboom, A.; Venitz, J.; Figg, W.O. "Rational Development of Histone Deacetylase Inhibitors as Anticancer Agents: A Review," *Mol. Pharmacol.*, 2005, 68, 917-932.
Ananthan, S. "Opioid Ligands With Mixed u/delta Opioid Receptor Interactions: An Emerging Approach to Novel Analgesics," *AAPS J.*, 2006, 8, E118-E125.
Anderson, S.; Komers, R. "Aliskiren Combined With Losartan in Diabetes and Nephropathy-To the Editors," *N. Engl. J. Med.*, 2008, 359, 1068-1070.
Ankarcrona, M.; Dypbukt, J.M.; Bonfoco, E.; Zhivotovsky, B.; Orrenius, S.; Lipton, S.A.; Nicotera, P. "Glutamate-Induced Neuronal Death: A Succession of Necrosis or Apoptosis Depending on Mitochondrial Function" *Neuron.* 1995, 15, 961-973.
Atkins, H. "Portfolio Optimization—Tying Down Gulliver: The Cannabinoid Therapy Market," *Specialtypharma*, 2005, 1, 34-38.
Baran, E.J. "Metal Complexes of Carnosine," *Biochem.* (Moscow), 1999, 65, 789-797.
Begon, S.; Pickering, G.; Eschalier, A.; Dubray, C. "Magesium Increases Morphine Analgesic Effect in Different Experimental Models of Pain," *Anesthesiology*, 2002, 96, 627-632.
Berkley, K.J. "Chapter 21—Visceral Nociception and Pain," *Core Topics in Pain*, (Holdcroft, A.J., Jagger, S. eds.) Cambridge University Press: United Kingdom, 2005, 145-150.
Bhalla, K.; List, A. "Histone Deacetylase Inhibitors in Myelodysplastic Syndrome," *Best Pract. Res. Clin. Haematol.*, 2004, 17, 595-611.
Bhattacharya, P.K. *Metal Ions in Biochemistry, Alpha Science International Ltd.*, 2005, Harrow. U.K., 16-65.
Borman, S. "Drugs From Academia—Some Drug Discovery Efforts Are Anything But 'Academic'."*Science & Technology*, 2007, 85, 42-47.
Buvanendran, A.; McCarthy, R.J.; Kroin, J.S.; Leong, W.; Perry, P.; Tuman, K.J. "Intrathecal Magnesium Prolongs Fentanyl Analgesia: A Prospective, Randomized, Controlled Trial," *Anesth. Analg.*, 2002, 95, 661-666.
Calabresi, P.; Marti, M.; Picconi, B.; Saulle, E.; Costa, C.; Centonze D.; Pisani, F.; Bernardi, G. "Lamotrigine and Remacemide Protect Striatal Neurons Against In Vitro Ischemia: An Electrophysiological Study," *Exp. Neurol.*, 2003, 182, 461-469.
Campos, A.R.; Santos, F.A.; Rao, V.S. "Ketamine-Induced Potentiation of Morphine Analgesia in Rat Tail-Flick Test: Role of Opioid-, $\alpha_2$-Adrenoceptors and ATP-Sensitive Potassium Channels," *Biol. Pharm. Bull.*, 2006, 29, 86-89.
Chen, C.D.; Welsbie, D.S.; Tran, C.; Baek, S.H.; Chen, R.; Vessella, R.; Rosenfeld, M.G.; Sawyers, C.L. "Molecular Determinants of Resistance to Antiandrogen Therapy," *Nat. Med.*, 2004, 10, 33-39.
Chez, M.G.; Burton, Q.; Dowling, T.; Chang, M.; Khanna, P.; Kramer, C. "Memantine as Adjunctive Therapy in Children Diagnosed With Autistic Spectrum Disorders: An Observation of Initial Clinical Response and Maintenance Tolerability," *J. Child Neurol.*, 2007, 22, 574-579.
Clarke, C.E.; Cooper, J.A.; Holdich, T.A.H. "A Randomized, Double-Blind, Placebo-Controlled, Ascending-Dose Tolerability and Safety Study of Remacemide as Adjuvant Therapy in Parkinson's Disease With Response Fluctuations," *Clin. Neuropharmacol.*, 2001, 24, 133-138.
Collier, H.O.J.; Francis, D.L.; Henderson, G.; Schneider, C. "Quasi Morphine-Abstinence Syndrome," *Nature*, 1974, 249, 471-473.
Corbett, A; McKnight, S.; Henderson, G. "Opioid Receptors," http://opioids.com/receptors/index.html, printed from internet Apr. 21, 2011, 10 pages.
Craft, R.M.; Leitl, M.D. "Potentiation of Morphine Antinociception by Pentobarbital in Female vs. Male Rats," *Pain*, 2006,121, 115-125.

de Ruijter, A.J.M.; van Gennip, A.H.; Caron, H.N.; Kemp, S.; van Kuilenburg, A.B.P. "Histone Deacetylases (HDACs): Characterization of the Classical HDAC Family," *Biochem. J.*, 2003, 370, 737-749.
Di Napoli, M.; Shah, I.M.; Stewart, D.A. "Molecular Pathways and Genetic Aspects of Parkinson's Disease: From Bench to Bedside," *Expert Rev. Neurother.*, 2007, 7, 1693-1729.
Diaz, M.; Patterson, S.G. "Management of Androgen-Independent Prostate Cancer," *Cancer Control*, 2004, 11, 364-373.
Diem, R.; Säther, M.B.; Merkler, D.; Demmer, I.; Maier, K.; Stadelmann, C.; Ehrenreich, H.; Bähr, M. "Combined Therapy With Methylprednisolone and Erythropoietin in a Model of Multiple Sclerosis," *Brain*, 2005, 128, 375-385.
D'Souza, D.C.; Charney, D.; Krystal, J. "Glycine Site Agonists of the NMDA Receptor: A Review," *CNS Drug Reviews*, 1995, 1, 227-260.
Encarnacion, E.V.; Hauser, R.A. "Considerations in Neuroprotection in Parkinson's Disease," *Medscape Neurology and Neurosurgery*, 2007, www.medscape.com/viewarticle/563258.
Fernandez, F.; Morishita, W.; Zuniga, E.; Ngyuen, J.; Blank, M.; Malenka, R.C.; Garner, C.C. "Pharmacotherapy for Cognitive Impairment in a Mouse Model of Down Syndrome," *Nat. Neurosci.*, 2007, 10, 411-413.
Fischer, A.; Sananbenesi, F.; Wang, X.; Dobbin, M.; Tsai, L-H. "Recovery of Learning and Memory is Associated With Chromatin Remodeling." *Nature*, 2007, 447, 178-183.
Friderichs, E. "Introduction," *Analgesics: From Chemistry and Pharmacology to Clinical Application*, (Buschmann, H.; Christoph, T.; Friderichs, E.; Maul, C.; Sundermann, B. eds.) Wilev-VCH Verlag GmbH & Co. KGaA: Federal Republic of Germany, 2002, 127-150.
Futaki, S.; Niwa, M.; Nakase, I.; Tadokoro, A.; Zhang, Y.; Nagaoka, M.; Wakako, N.; Sugiura, Y. "Arginine Carrier Peptide Bearing Ni(II) Chelator to Promote Cellular Uptake of Histidine-Tagged Proteins," *Bioconjuq. Chem.*, 2004, 15, 475-481.
Gonsette, R. E. "Combination Therapy for Multiple Sclerosis," *Int. MS J.*, 2004, 11, 10-21.
Greenamyre, J.T.; Eller, R.V.; Zhang, Z.; Ovadia, A.; Kurian, R.; Gash, D.M. "Antiparkinsonian Effects of Remacemide Hydrochloride, a Glutamate Antagonist, in Rodent and Primate Models of Parkinson's Disease," *Ann. Neurol.*, 1994, 35, 655-661.
Hemby, S.E.; Co, C.; Dworkin, S.I.; Smith, J.E. "Synergistic Elevations in Nucleus Accumbens Extracellular Dopamine Concentrations During Self-Administration of Cocaine/Heroin Combinations (Speedball) in Rats," *J. Pharmacol. Exp. Ther.*, 1999, 288, 274-280.
Isaacson, S. "Current Medical Treatment of Parkinson Disease," *Evolving Concepts in Parkinson Disease, Pathophysiology, Diagnosis, and Treatment*, 2007, 4-6.
Jones, C.E.; Taylor, P.J.; McEwan, A.G.; Hanson, G.R. "Spectroscopic Characterization of Copper(II) Binding to the Immunosuppressive Drug Mycophenolic Acid," *J. Am. chem .. Soc.*, 2006, 128, 9378-9386.
Kang, J.H. "Protection by Carnosine and Homocarnosine Against L-Dopa-Fe(III)-Mediated DNA Cleavage." *Bull. Korean Chem. Soc.*, 2005, 26, 1251-1254.
Kappos, L.; Antel, J.; Comi, G.; Montalban, X.; O'Connor, P.; Polman, C.H.; Haas, T.; Korn, A.A.; Karlsson, G.; Radue, E.W. "Oral Fingolimod (FTY720) for Relapsing Multiple Sclerosis," *N. Engl. J. Med.*, 2006, 355, 1124-1140.
Kaur, S.; Starr, M.S. "Differential Effects of Intrastriatal and Intranigral Injections of Glutamate Antagonists on Motor Behaviour in the Reserpine-Treated Rat," *Neuroscience*, 1997, 76, 345-354.
Keith, D.E.; Anton, B.; Murray, S.R.; Zaki, P.A.; Chu, P.C.; Lissin, D.V.; Monteillet-Agius, G.; Stewart, P.L.; Evans, C.J.; Von Zastrow, M. "µ-Opioid Receptor Internalization: Opiate Drugs Have Differential Effects on a Conserved Endocytic Mechanism in Vitro and in the Mammalian Brain." *Mol. Pharmacol.*, 1998, 53, 377-384.
Kemp, J.A.; McKernan, R.M. "NMDA Receptor Pathways as Drug Targets," *Nat. Neurosci.*, 2002, 5, 1039-1042.
Klopman, G.; Sedykh, A. "An MCASE Apprach to the Search of a Cure for Parkinson's Disease." *BMC Pharmacal.*, 2002, 2, 8.
Kohl, B.K.; Dannhardt, G. "The NMDA Receptor Complex: A Promising Target for Novel Antiepileptic Strategies," *Curr. Med. Chem.*, 2001, 8, 1275-1289.

(56) References Cited

OTHER PUBLICATIONS

Kreek, M.J. "Chapter 104: Molecular and Cellular Neurobiology and Pathophysiology of Opiate Addiction," *Neuropsychopharmacology: The Fifth Generation of Progress*, American College of Neuropsychopharmology, 2002, 1491-1506.

Krier, M.; de Araujo-Junior, J.X.; Schmitt, M.; Duranton, J.; Justiano-Basaran, H.; Lugnier, C.; Bourguignon, J-J.; Rognan, D. "Design of Small-Sized Libraries by Combinatorial Assembly of Linkers and Functional Groups to a Given Scaffold: Application to the Structure-Based Optimization of Phosphodiesterase 4 Inhibitor," *J. Med. Chern.*, 2005, 48, 3816-3822.

Kroin, J.S.; Buvanendran, A.; Beck, D.R.; Topic, J.E.; Watts, D.E.; Tuman, K.J. "Clonidine Prolongation of Lidocaine Analgesia After Sciatic Nerve Block in Rats is Mediated Via the Hyperpolarization-Activated Cation Current, Not by α-Adrenoreceptors," *Anesthesiology*, 2004, 101, 488-494.

Kroin, J.S.; Buvanendran, A.; McCarthy, R.J.; Hemmati, H.; Tuman, K.J. "Cyclooxygenase-2 Inhibition Potentiates Morphine Antinociception at the Spinal Level in a Postoperative Pain Model." *Reg. Anesth. Pain Med.*, 2002, 27, 451-455.

Krymchantowski, A.V.; Rapoport, A.M.; Jevoux, C.C. "The Future of Acute Care and Prevention in Heachache," *Neural. Sci.*, 2007, 28 Suppl 2, 8166-8178.

Larner, J.; Price, J.D.; Heimark, D.; Smith, L.; Rule, G.; Piccariello, T.; Fonteles, M.C.; Pontes, C.; Vale, D.; Huang, L. "Isolation, Structure, Synthesis, and Bioactivity of a Novel Putative Insulin Mediator. A Galactosamine chiro-Inositol Pseudo-Disaccharide $Mn^{2+}$ Chelate With Insulin-like Activity," *J. Med. Chem.*, 2003, 46, 3283-3291.

Leach, J.P.; Girvan, J.; Jamieson, V.; Jones, T.; Richens, A.; Brodie, M.J. "Lack of Pharmacokinetic Interaction Between Remacemide Hydrochloride and Sodium Valproate in Epileptic Patients." *Seizure*, 1997, 6, 179-184.

Leach, J.P.; Girvan, J.; Jamieson, V.; Jones, T.; Richens, A; Brodie, M.J. "Mutual Interaction Between Remacemide Hydrochloride and Phenytoin." *Epilepsv Res.*, 1997, 26, 381-388.

Lin, C-R.; Yang, L-C.; You, H-L.; Lee, C-T.; Tai, M-H.; Tan, P-H.; Lin, M-W.; Cheng, J-T. "Antinociceptive Potentiation and Attenuation of Tolerance by Intrathecal Electric Simulation in Rats," *Anesth. Analg.*, 2003, 96, 1711-1716.

Lipton, SA "Prospects for Clinically Tolerated NMDA Antagonists: Open-Channel Blockers and Alternative Redox States of Nitric Oxide," TINS, 1993, 16,527-532.

Lyden, P.; Wahlgren, N.G. "Mechanisms of Action of Neuroprotectants in Stroke," *J. Stroke Cerebrovasc. Dis.*, 2000, 9, 9-14.

Ma, Z.; Han, S.; Kravtsov, V.C.; Moulton, B. "Conformational Isomerism and Hydrogen-Bonded Motifs of Anion Assisted Supramolecular Self-Assemblies Using Cu"/Co" Salts and Pvridine-4-Acetamide," *Inorganica Chimica Acta*, 2010, 363, 387-394.

Ma, Z.; Hopson, R.; Cai, C.; Han, S.; Moulton, B. "Modifying Lipophilicities of Zn(II) Coordination Species by Introduction of Ancillary Ligands: A Supramolecular Chemistry Approach," *Crystal Growth & Design*, 2010, 10, 2376-2381.

Ma, Z.; Moulton, B. "Mixed-Ligand Coordination Species: A Promising Approach for 'Second-Generation' Drug Development," *Crystal Growth & Design*, 2007, 7, 196-198.

Ma, Z.; Moulton, B. "Recent Advances of Discrete Coordination Complexes and Coordination Polymers in Drug Delivery," *Coordination Chemistry Reviews*, 2011, Article in Press, 19 pages.

Ma, Z.; Moulton, B. "Supramolecular Medicinal Chemistry: Mixed-Ligand Coordination Complexes," *Molecular Pharmaceutics*, 2007, 4, 373-385.

Maggio, S.C.; Rosato, RR; Kramer, L.B.; Dai, Y. Rahmani, M.; Paik, D.S.; Czarnik, A.C.; Payne, S.; Spiegel, S.; Grant, S. "The Histone Deacetylase Inhibitor MS-275 Interacts Synergistically With Fludarabine to Induce Apoptosis in Human Leukemia Cells," *Cancer Res.*, 2004, 64, 2590-2600.

Marino, M.J.; Valenti, 0.; Conn, P.J. "Glutamate Receptors and Parkinson's Disease: Opportunities for Intervention." *Drugs Aging*, 2003, 20, 377-397.

Miller, S.; Heurtaux, D.; Baati, T.; Horcajada, P.; Greneche, J-M.; Serre, C. "Biodegradable Therapeutic MOFs for the Delivery of Bioactive Molecules," *Chem. Commun.*, 2010, 46, 4526-4528.

Minucci, S.; Pelicci, P.G. "Histone Deacetylase Inhibitors and the Promise of Epigenetic (and More) Treatments for Cancer" *Nat. Rev. Cancer*, 2006, 6, 38-51.

Missale, C.; Fiorentini, C.; Busi, C.; Collo, G.; Spano, P.F. "The NMDAID1 Receptor Complex as a New Target in Drug Development," *Current Topics in Medicinal Chemistry*, 2006, 6, 801-808.

Morelli, M.; Fenu, S.; Pinna, A; Di Chiara, G. "Opposite Effects of NMOA Receptor Blockade on Dopaminergic $D_1$- and $D_2$-Mediated Behavior in the 6-Hydroxydopamine Model of Turning: Relationship with c-fos Expression," *J. Pharmacol. Exp. Ther.*, 1992, 260, 402-408.

Moulton, B.; Zaworotko, M.J. "From Molecules to Crystal Engineering: Supramolecular Isomerism and Polymorphism in Network Solids," *Chem. Rev.*, 2001, 101, 1629-1658.

Napolitano, A; Pezzella, A; Misuraca, G.; Prota, G. "New Directions in Parkinson's Research and Treatment," *Expert Opinion on Therapeutic Patents*, 1998, 8, 1251-1268.

Nestler, E.J.; Aghajanian, G.K. "Molecular and Cellular Basis of Addiction," Science, 1997, 278, 58-63.

Nicholas, A. "Pathophysiology and Diagnosis of Parkinson Disease," *Evolving Concepts in Parkinson Disease Pathophysiology, Diagnosis and Treatment*, 2007, 1-3.

Paintlia, A.S.; Paintlia, M.K.; Singh, I.; Singh, A.K. "Immunomodulatory Effect of Combination Therapy with Lovastatin and 5-Aminoimidazole-4-Carboxamide-1-β-D-Ribofuranoside Alleviates Neurodegeneration in Experimental Autoimmune Encephalomyelitis," *Am. J. Pathol.*, 2006, 169, 1012-1025.

Palmer, G.C. "Neuroprotection by NMDA Receptor Antagonists in a Variety of Neuropathologies," *Curr. Drug Targets*, 2001, 2, 241-271.

Parsons, C.G. "NMDA Receptors as Targets for Drug Action in Neuropathic Pain," *Eur. J. Pharmacal.*, 2001, 429, 71-78.

Parsons, C.G.; Danysz, W.; Quack, G. "Glutamate in CNS Disorders as a Target for Drug Development: An Update," *Drug News Perspect.*, 1998, 11, 523-569.

Petrenko, A.B.; Yamakura, T.; Baba, H.; Shimoji, K. "The Role of N-Methyl-D-Aspartate (NMDA) Receptors in Pain: A Review," *Anesth. Analg.*, 2003, 97, 1108-1116.

Pool, J.L. "Direct Renin Inhibition: Focus on Aliskiren," *J. Manag. Care Pharm.*, 2007, 13, 821-833.

Posey, D.J.; Kern, D.L.; Swiezy, N.B.; Sweeten, T.L.; Wiegand, R.E.; McDougle, C.J. "A Pilot Study of D-Cycloserine in Subjects With Autistic Disorder," *Am. J. Psychiatry*, 2004, 161, 2115-2117.

"Psycological and Physiological Consequences of Noncompetitive Antognosim of the NMDA Receptor by Ketamine," Category: Neurochemistry, Term Paper Code: 819, http://sulcus.berkeley.edu/mcb/165001/papers/manuscripts/819.html, 6 pages.

Rao, J. "Advances in the Treatment of Parkinson Disease," *Evolving Concepts in Parkinson Disease Pathophysiology, Diagnosis, and Treatment*, 2007, 10-13.

Rezai-Zadeh, K.; Shytle, D.; Sun, N.; Mori, T.; Hou, H.; Jeanniton, D.; Ehrhart, J.; Townsend, K.; Zeng, J.; Morgan, D.; Hardy, J.; Town, T.; Tan, J. "Green Tea Epigallocatechin-3-Gallate (EGCG) Modulates Amyloid Precursor Protein Cleavage and Reduces Cerebral Amyloidosis in Alzheimer Transgenic Mice," *J. Neurosci.*, 2005, 25, 8807-8814.

Rorick-Kehn, L.M.; Johnson, B.G.; Burkey, J.L.; Wright, R.A.; Calligaro, D.O.; Marek, G.J.; Nisenbaum, E.S.; Catlow, J.T.; Kingston, A.E.; Giera, D.D.; Herin, M.F.; Monn, J.A.; McKinzie, D.L.; Schoepp, D.D. "Pharmacological and Pharmacokinetic Properties of a Structurally Novel, Potent, and Selective Metabotropic Glutamate 2/3 Receptor Agonist: In Vitro Characterization of Agonist (−)-(1R,4S,5S,6S)-4-Amino-2-sulfonylbicyclo[3.1.0]-hexane-4,6-dicarboxylic Acid (LY404039)," *J. Pharmacol. Exp. Ther.*, 2007, 321, 308-317.

Rosato, R.R.; Almenara, J.A.; Dai, Y.; Grant, S. "Simultaneous Activation of the Intrinsic and Extrinsic Pathways by Histone Deacetylase (HDAC) Inhibitors and Tumor Necrosis Factor-Related Apoptosis-Inducing Ligand (TRAIL) Synergistically Induces

(56) References Cited

OTHER PUBLICATIONS

Mitochondrial Damage and Apoptosis in Human Leukemia Cells," *Mol. Cancer. Ther.*, 2003, 2, 1273-1284.

Salama, H.H.; Kolar, O.J.; Zang, Y.C.Q; Zhang, J. "Effects of Combination Therapy of 8etalnterferon la and Prednisone on Serum Immunologic Markers in Patients with Multiple Sclerosis," *Mult. Seler.*, 2003, 9, 28-31.

Sandborn, W.J. "Oral 5-ASA Therapy in Ulcerative Colitis: What Are the Implications of the New Formulations?" *J. Clin. Gastroenterol.*, 2008, 42, 338-344.

Sartor, R.B. "Mechanisms of Disease: Pathogenesis of Crohn's Disease and Ulcerative Colitis," *Nat. Clin. Pract. Gastroenterol. Hepatol.*, 2006, 3, 390-407.

Sathyan, G.; Zomorodi, K.; Gidwani, S.; Gupta, S. "The Effect of Dosing Frequency on the Pharmacokinetics of a Fentanyl HC1 Patient-Controlled Transdermal System (PCTS)," *Clin. Pharmacokinet.*, 2005, 44 Sup! 1, 17-24.

Schnitzer, T.J. "Pain Management Today—Optimising the BenefiURisk Ratio: Defining the Role of Weak Opioids and Combination Analgesics," *Clin. Rheumatol.*, 2006, 25 *Suppl1*, S1.

Seeburg, P.H.; Burnashev, N.; Kohr, G.; Kuner, T.; Sprengel, R.; Monyer, H. "The NMDA Receptor Channel: Molecular Design of a Coincidence Detector," *Recent Prog. Horm. Res.*, 1995, 50, 19-34.

Shoulson, I.; Penney, J.; McDermott, M.; Kieburtz, K.; Schwid, S.; Kayson, E; Chase, T.; Fahn, S.; Greenamyre, J.T.; Lang, A; Siderowf, A; Pearson, N.; Harrison, M.; Rost-Ruffner, E; Colcher, A; Lloyd, M.; Matthews, M.; Pahwa, R; McGuire, D.; Lew, M.F.; Schuman, S.; Marek, K.; Broshjeit, S.; Factor, S.; Brown, D.; Feigin, A; Mazurkiewicz, J.; Ford, B.; Jennings, D.; Dillon, S.; Comella, C.; Blasucci, L.; Janko, K., Shulman, L., Wiener, W.; Bateman-Rodriguez, D.; Carrion, A; Suchowersky, 0.; Lafontaine, AL.; Pantella, C.; Siemers, E; Belden, J.; Davies, R; Lannon, M.; Grimes, D.; Gray, P.; Martin, W.; Kennedy, L.; Adler, C.; Newman, S.; Hammerstad, J.; Stone, C.; Lewitt, P.; Bardram, K.; Mistura, K.; Miyasaki, J.; Johnston, L.; Cha, J-H. J.; Tennis, M.; Panisset, M.; Hall, J.; Tetrud, J.; Friedlander, J.; Hauser, R; Gauger, L.; Rodnitzky, R; Deleo, A; Dobson, J.; Seeberger, L.; Dingmann, C.; Tarsy, D.; Ryan, P.; Elmer, L.; Ruzicka, D.; Stacy, M.; Brewer, M.; Locke, B.; Baker, D.; Casaceli, C.; Day, D.; Florack, M.; Hodgeman, K.; Laroia, N.; Nobel, R; Orme, C.; Rexo, L.; Rothenburgh, K.; Sulimowicz, K.; Watts, A; Wratni, E; Tariot, P.; Cox, C.; Leventhal, C.; Alderfer, V.; Craun, AM.; Frey, J.; McCree, L.; McDermott, J.; Cooper, J.; Holdich, T.; Read, B. "A Randomized, Controlled Trial of Remacemide of Motor Fluctuations in Parkinson's Disease," *Neurology*, 2001, 56, 455-462.

Stillman, M. "Clinical Approach to Patients With Neuropathic Pain," *Cleve. Clin. J. Med.*, 2006, 73, 726-739.

Suginoshita, Y.; Tabata, Y.; Moriyasu, F.; Ikada, Y.; Chiba, T. "Liver Targeting of Interferon-B With a Liver-Affinity Polysaccharide Based on Metal Coordination in Mice," *J. Pharmacal. Exp. Ther.*, 2001. 298. 805-811.

Surmeier, D.J. "Calcium, Ageing, and Neuronal Vulnerability in Parkinson's Disease," *Lancet Neural.*, 2007, 6, 933-938.

Tagliati, M. "Carbidopa-Levodopa Orally Disintegrating Tablets," Evolving Concepts in *Parkinson Disease Pathopysiology*, Diagnosis, and Treatment, 2007, 7-9.

"Tekturna (aliskiren) Tablets 150mg-300mg," MedScape from WebMD, http://www.medscape.com/infosite/tekturna/article-pharmacology, 3 pgs.

Thomas, R.J. "Excitatory Amino Acids in Health and Disease," JAGS, 1995, 43, 1279-1289.

Tsien, J.Z. "Linking Hebb's Coincidence-Detection to Memory Formation," *Curr. Opin. Neurobiol.*, 2000, 10, 266-273.

Tullman, M.J.; Lublin, F.D. "Combination Therapy in Multiple Sclerosis," *Curr. Neural. Neurosci. Rep.*, 2005, 5, 245-248.

Unterwald, E.M.; Anton, B.; To, T.; Lam, H. Evans, C.J. "Quantitative Immunolocalization of Mu Opioid Receptors: Regulation by Naltrexone," *Neuroscience*, 1998, 85, 897-905.

Watters, J.I.; DeWitt, R. "The Complexes of Nickel(II) Ion in Aqueous Solutions Containing Oxalate Ion and Ethylendeiamine," *J. Am. Chem. Soc.*, 1960, 82, 1335-1339.

Weinstock-Guttman, B.; Bakshi, R. "Combination Therapy for Multiple Scelerosis: The Treatment Strategy of the Future?" *CNS Drugs*, 2004,18, 777-792.

Wilson, J.F. "The Pain Divide Between Men and Women," *Ann. Intern. Med.*, 2006, 144, 461-464.

Zhu, Y-Y.; Zhu-Ge, Z-B.; Wu, D-C.; Wang, S.; Liu, L-Y.; Ohtsu, H.; Chen, Z. "Carnosine Inhibits Pentylenetetrazol-Induced Seizures by Histaminergic Mechansims in Histidine Decarboxylase Knock-Out Mice," *Nerosci. Lett.*, 2007, 416, 211-216.

Farkas et al., Journal of Chemical Society, Dalton Transactions, pp. 1545-1551 (1983).

Crabtree, R., "The Organometallic Chemistry of the Transition Metals," John Wiley & Sons Inc., NY, NY (3$^{rd}$ edition) (2001).

US 8,716,300 B2

FREQUENCY MODULATED DRUG DELIVERY (FMDD)

REFERENCE TO EARLIER FILED APPLICATIONS

The present application is a continuation of U.S. patent application Ser. No. 12/316,259, filed Dec. 9, 2008, which is hereby incorporated by reference in its entirety.

BACKGROUND OF THE INVENTION

Combination drug therapy has become a critical tool in the treatment of many disease states. Using two or more therapeutic agents with complementary mechanistic actions has been shown to hasten the resolution and reduce the severity of certain disease states more effectively than is possible with either agent alone. While exploiting the potential synergies between the agents and minimizing their side effects has always been the goal of combination drug therapy, combination strategies have also been shown to lower treatment failure, case-morbidity and mortality rates, slow the development of resistant or refractory cases, lower overall healthcare costs, and improve patients' overall quality of life. As our knowledge of the mechanisms of disease expands, advanced combination therapeutic strategies can improve the outcome of pharmaceutical intervention in these disease states.

SUMMARY OF THE INVENTION

Embodiments of the present disclosure include a coordination complex, also known as a coordination compound, comprising a first biologically active moiety, a second biologically active moiety, and a metal, wherein the first biologically active moiety and second biologically active moiety are each bound to the metal by at least one binding site, wherein the first biologically active moiety and second biologically active moiety are different, and wherein the first biologically active moiety and the second biologically active moiety both have a biological effect on a target tissue.

Other embodiments include a method for enhancing pharmacodynamic properties of biologically active moieties, by forming a coordination complex comprising a first biologically active moiety, a second biologically active moiety, and a metal, wherein the first biologically active moiety and the second biologically active moiety are each bound to the metal by at least one binding site, and wherein the first biologically active moiety and the second biologically active moiety are different.

Further embodiments of the present disclosure include a method of treatment, including administering a coordination complex comprising at least a first biologically active moiety, a second biologically active moiety, and a metal, wherein the first biologically active moiety and the second biologically active moiety both have a biological effect on a target tissue.

BRIEF DESCRIPTION OF THE FIGURES

For a better understanding of the embodiments of the present disclosure, reference is made to the figures contained herein.

DETAILED DESCRIPTION OF THE INVENTION

Figure 1:
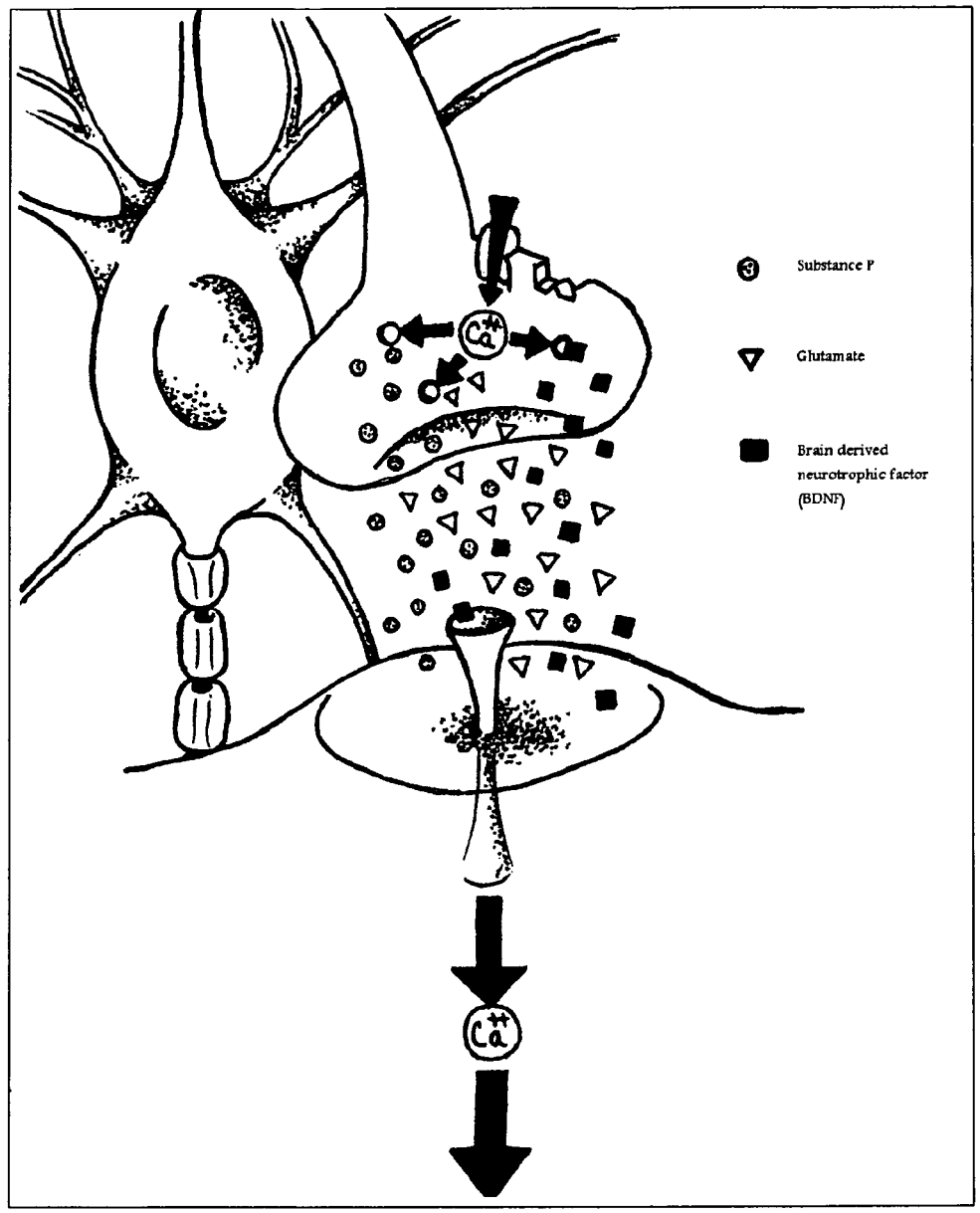
FIG. 1 illustrates that pain transmission can occur through voltage-dependant calcium channels releasing neurotransmitters (Glu, Substance P and BDNF), which activates the NMDA receptor and propagating the pain signal.

In many combination pharmaceutical applications, simultaneously delivering two or more pharmaceutical agents in a kinetically or frequency modulated synergistic manner may further potentiate the beneficial effects of the respective agents. This synergistic delivery may be facilitated if the respective agents were introduced into the body as a single integral molecular entity.

Simply delivering a combination drug as a single molecular entity, however, does not ensure efficacy. For example, when pullalan and interferon were covalently bound into a single molecule, the pullalan portion of the conjugated drug interfered with the binding of interferon to the liver cell surface receptor, thereby preventing induction of the antiviral enzyme, 2-5AS and rendering the conjugated drug ineffective against hepatitis. (Y. Suginoshita et al., Liver Targeting of Interferon—with a Liver-Affinity Polysaccharide Based on Metal Coordination in Mice, J. Pharmacol. Exp. Ther., 2001, 298 (2), 805-811).

Only when the two were combined as a metal complex did interferon bind effectively to cell surface receptor, while still retaining the liver targeting properties provided by the pullalan moiety. This notion of combining agents as metal complexes is further supported by the complexation of polyarginine and a peptide analog with nickel to create a peptide with enhanced cellular transfection efficiency. (S. Futaki et al., Arginine Carrier Peptide Bearing Ni(II) Chelator to Promote Cellular Uptake of Histidine-Tagged Proteins, Bioconjug Chem, 2004, 15 (3), 475-81). These examples show that a bond between a metal and pharmaceutical ligand can both impart the thermodynamic stability necessary to deliver the drug to its target and be labile enough to allow the drug to retain its biological activity.

Approaches to facilitate the delivery of the combination products have focused on the process known as co-crystallization. By and large, the advantages that co-crystals provide to the pharmaceutical compounds include improved solubility, bioavailability, stability and hygroscopicity. The vast majority of the co-crystallization processes rely on hydrogen bonding, Van der Waal forces, ionic bonding and lipophilic interactions between the components of the co-crystal. In only one example is metal coordination chemistry, namely (ibuprofen)$_4$Cu$_2$(caffeine)$_2$, utilized to facilitate the formation of co-crystals of pharmaceutical agents. (Zhenbo Ma & Brian Moulton, Supramolecular Medicinal Chemistry: Mixed-Ligand Coordination Complexes, Molecular Pharmaceutics, 2007, 4(3), 373-385).

The concept of combining pharmacophore fragments into a single molecular entity is a novel approach to combination pharmaceutical products. This approach relies on in silico techniques to design the molecular scaffold that retains the therapeutic portions of the pharmaceutical components, while eliminating the toxic parts. To the best of our knowledge, no examples of using metals to combine the different pharmacophore fragments have been reported.

The present disclosure contemplates administration of pharmaceutical or biologically active agents in a manner known as "frequency modulated drug delivery," or "FMDD." FMDD is a method whereby a combination of biologically active agents, which can potentiate or have a positive impact on the respective pharmacodynamics or biological effects, are delivered in such a manner that the respective kinetics are synergistically optimized. This kinetic synergy is best accomplished when the two biologically active agents are part of the same molecule. In that way, delivery to various tissue loci or the same tissue loci is greatly facilitated. FMDD is further defined by the method of synergistically delivering the biologically active agents such that the two biologically active agents are part of the same molecule yet still have the capacity to interact with their respective receptors with minimum interference from the other biologically active agent. Thus, as an embodiment of this invention, the FMDD composition is two biologically active agents that are combined as a single molecular entity through metal coordination complexation such that the two biologically active agents are delivered to a target tissue in a kinetically synergistic manner. This kinetic synergy may be increased over two biologically active moieties that are introduced together but are not part of the same complex.

In embodiments of the coordination complexes described herein, the first biologically active moiety and the second biologically active moiety both have a biological effect on a target tissue, which may or may not be the same tissue. In certain embodiments, however, both the first biologically active moiety and the second biologically active moiety do have a biological effect on a same target tissue. In some embodiments, the first biologically active moiety and the second biologically active moiety have a biological effect on a tissue associated with the same disease state, though the two moieties may not have a biological effect on the same tissue. In other embodiments, though, the first biologically active moiety and the second biologically active moiety do have a biological effect on a same target tissue associated with a disease state.

In certain embodiments of the coordination complexes described herein, the first biologically active moiety and the second biologically active moiety have a biological effect on receptors on a tissue associated with the same disease state, though the first and second moieties may not have an effect on the same tissue, and may or may not have an effect on the same receptors. In other embodiments, both the first biologically active moiety and the second biologically active moiety have a biological effect on the same receptors on the same tissue associated with a same disease state. In still other embodiments, both the first biologically active moiety and the second biologically active moiety have a biological effect on different receptors on the same tissue associated with a same disease state.

In other embodiments of the coordination complexes described herein, the metal itself also has a biological effect on a target tissue. In some embodiments, the metal potentiates the biological effect of at least one of the first biological moiety and the second biological moiety.

Certain embodiments of the present disclosure include a coordination complex, comprising a first biologically active moiety, a second biologically active moiety, and a metal, wherein the first biologically active moiety and second biologically active moiety are each bound to the metal by at least one binding site, and wherein the first biologically active moiety and second biologically active moiety are different. The first biologically active moiety may potentiate the biological effect of the second biologically active moiety. This potentiating effect may be due to the increased kinetic synergy as a result of their inclusion in a coordination complex.

Coordination Complex

This invention concerns coordination complexes having the formula:

$$L_2\text{-}M\text{-}L_1$$

wherein M is a suitable metal and each of L1 (ligand 1) and L2 (ligand 2) is a pharmaceutical or biologically active agent or its anion formed by reaction of the agent with a base. In the complex, L1 and L2 are bound to M by covalent coordination bonds and L1 and L2 are different from each other. As such, the compounds ML1 L2 constitute mixed ligand complexes (also called hetero-ligated complexes or compounds). Suitable metals include, but are not limited to, Mg, Ca, Sr, Fe, Co, Ni, Cu, Zn, Pd, Pt, Ru, Rh, Al, and Sn.

The term "complex" in chemistry, also called a "coordination compound" or "metal complex", includes a structure consisting of a central atom or molecule, a metal, connected to surrounding atoms or molecules. The ions or molecules surrounding the metal are called ligands. Ligands are generally bound to a metal ion through binding sites of the ligand by a coordinate covalent bond (donating electrons from a lone electron pair into an empty metal orbital), and are thus said to be coordinated to the ion. Coordination complexes typically have stability constants that fall between those of salts and classic covalent bonds. The stability of coordination complexes relies on the nature of the metal and the ligands attached to the metal. Ligands with one binding site are called monodentate ligands. Ligands that can bond to a metal atom through two or more binding sites or donor atoms participate in ring closure at the metal center. These ligands are known as ambidentate ligands, and the compounds formed are known as chelation compounds. Chelation involves coordination of more than one sigma-electron pair donor group from the same ligand to the same metal atom. As such, chelation compounds are a subset of coordination compounds. Chelation is a critical component in the stabilization of a coordination compound. Within the s-block elements, this is particularly true for magnesium and calcium. For example, the log $K_{eq}$ of the acetic acid-magnesium complex is 0.47. With the incorporation of an additional chelating atom, nitrogen, the complex becomes glycine-magnesium and the log $K_{eq}$ increase to 1.34. Additional ligands, other than the initial ligand, can stabilize the metal-drug complex further. Adding salicylaldehyde to the glycine-magnesium complex, given by the reaction equilibrium $$Mg^{2+} + SA^- + G^- \leftrightarrow Mg(SA)(G)$$

further increases the log $K_{eq}$ to 4.77. Clearly salicylaldehyde adds a stabilizing effect to the magnesium glycine bond. This stabilizing effect is also imparted by other chelating ligands such as dipyridyl or ethylene diamine and N-alkyl analogs thereof.

Simple combinations of metals with ligands in solution do not always produce the same product. It is recognized that the salt of an organic acid is easily prepared by treating the acid with a base and a metal salt where the expected product is the metal salt of the organic acid; a method known by anyone skilled in the art. However, when coordination chemistry contributes to the bonding between the organic acid and the metal, a variety of conditions, such as solvent, temperature and, perhaps most importantly, ligands attached to the metal, impact the structure and the stability of the coordination complex.

The present disclosure is directed to coordination complexes for treatment of disease and medical conditions in animals, with humans being a preferred embodiment. In these embodiments, the ligands include biologically or pharmaceutically active agents or moieties. As used herein, a biologically or pharmaceutically active agent or moiety is an agent used to treat a disease or medical condition. Agents with potential for use in embodiments of the present disclosure may be referred to as frequency modulated drug delivery, or "FMDD," ligands. These FMDD ligands include the biologically or pharmaceutically active agent, and also any other linker molecules or other components needed to form the complex. The FMDD ligands include at least one binding site or donor atom. An FMDD ligand with one donor site is a monodentate FMDD ligand, and an FMDD ligand with more than one binding site or donor atom is an ambidentate FMDD ligand. A complex formed with FMDD ligands may be referred to as an FMDD complex. The FMDD complex may include the FMDD ligands, the metal, and any other ingredient or component that may not necessarily be bonded to the metal, yet is still part of the complex.

In the complexes L2-M-L1, L1 or L2 may have one donor group, called monodentate ligands. In other complexes, L1 or L2 may have more than one donor group and are thus capable of occupying more than one coordination site. These ambidentate ligands can function as a bridge between metal centers to form polynuclear or polymeric complexes, or participate in ring closure at a single metal center to form chelate complexes. This invention concerns coordination complexes of both types.

Coordination complexes with chelating ligands are thermodynamically more stable than those with similar ligands that do not chelate. Five- or six-membered chelate rings are the most favored in coordination compounds. But compounds forming four- seven- and eight- and larger membered rings may also be stable. Embodiments of this invention includes coordination complexes containing four- five- six- seven- and eight-membered rings.

The nature of the bond between the ligand and the metal in a coordination complex is covalent in nature. This is critical to the mechanism of the chemistry concertedly operating with the pharmacology described in this invention. A pure ionic bond, such as that which exists in a salt, will not retain the integrity of the molecule throughout the time course required for synergistic effects of the two or more respective ligands to be manifest. A bond between the ligands that is purely covalent would certainly survive the trials and travails inherent in the organism on its way to the target organ but would not be able to elicit the pharmacologic effects of both reagents if they were covalently tethered to each other. It is an embodiment of this invention that only a metal coordination complex possesses enough covalent bond strength to retain the integrity of the hetero-ligated complex in the body to the target site yet be labile enough to allow both biologically active agents to impart their pharmacologic effect at the target site.

In preparative coordination chemistry mixed-ligand complexes are often prepared by reaction of a metal with a mixture of L1 and L2 or their salts (eq 1); reaction of a metal with L1 or its salt, followed by addition and reaction of L2 or its salt (eq 2); or co-proportionation of homoleptic complexes (eq 3). This is shown below for the case of a divalent metal alkoxide reacting with HL1 and HL2:

$$M(OBu)_2 + HL_1 + HL_2 \rightarrow ML_1L_2 + 2BuOH \quad (eq\ 1)$$

$$M(OBu)_2 + HL_1 \rightarrow M(L_1)(OBu) + BuOH$$

$$M(L_1)(OBu) + HL_2 \rightarrow ML_1L_2 + BuOH \quad (eq\ 2)$$

$$M(L_1)_2 + M(L_2)_2 \rightarrow 2ML_1L_2 \quad (eq\ 3)$$

where Bu=butyl.

Mixed ligand complexes occur when a complex has two or more different ligands in its coordination sphere. There are a number of general synthetic approaches to prepare these compounds, which include: 1) Simultaneous combination of the two ligands; 2) Sequential combination of the ligands; and 3) A reproportionation reaction between two binary bis-ligand complexes.

$$M + L + L' \rightleftharpoons MLL' \quad (1)$$

$$ML + L' \rightleftharpoons MLL' \quad (2)$$

$$ML_2 + ML'_2 \rightleftharpoons 2MLL' \quad (3)$$

In a solution containing a metal ion and ligands L and L', the formation of the mixed ligand complex MLL' is more favored on a statistical basis, than the formation of the binary complexes ML2 and ML'2. The equilibrium constant for the formation of this mixed ligand complex is related to the equilibrium constant of the corresponding reproportionation reaction, $K_{reprop}$. If only statistical factors were responsible for formation of the mixed ligand complex, then $K_{reprop}=4$. As the experimental values of $K_{reprop}$ differ from the statistical value, other factors are involved in the formation of mixed ligand complexes. These factors can affect product formation by stabilizing or destabilizing the complexes, and include electronic, electrostatic, and steric effects. (P. K. Bhattacharya, Metal Ions in Biochemistry, Alpha Science International Ltd., 2005).

For example, the formation of an asymmetric metal coordination complex is favored thermodynamically, which is in part due to the increased degeneracy of the d-orbitals. (J. Watters & R. DeWitt, The Complexes of Nickel(II) Ion in Aqueous Solutions Containing Oxalate Ion and Ethylenediamine, J. of Am. Chem. Soc., 1959, 82, 7). The favored formation of monomomeric heteroligated metal coordination species was observed when a new ligand is added to homoligated dimeric metal coordination complex. The occupation of the available coordination sites in the homoligated species to produce a more asymmetric product was the apparent driving force for the formation of the heteroligated product. (E. J. Baran, Metal Complexes of Carnosine, Biochemistry, 1999, 65 (7), 11).

Substitution reactions, in which the ligand in a metal complex is replaced by a second ligand, are also used to prepare mixed ligand complexes.

$$ML_2 + L' \rightleftharpoons MLL' + L$$

These reactions depend not only on the thermodynamic stability of the ligand binding with the metal ion, but on the mechanism of the reaction. Preparation of mixed-ligand complexes involves precise control of the following reaction parameters: stoichiometry, solvent, temperature, concentration, order of addition of reagents, and isolation and purification of the mixed-ligand complex.

The selection of the metal is determined by the application (i.e. the disease state to be treated) and the nature of the drug ligands used in the application. For drug ligands containing functional groups rich in oxygen (carboxylic acids, amides, esters, alcohols, ethers, etc) metals of Group IIA, Group IIIB, and Group IVB are likely metals of choice. Magnesium and calcium are preferred metals of this invention due to their generally regarded safety. For drug ligands containing nitrogen (amines, amides, etc) transition metals are likely metals of choice.

Coordination can be confirmed and differentiated from mixtures of components or formation of simple salts, by a variety of methods including:
1. $^1H$ and $^{13}C$ nuclear magnetic resonance spectroscopy, through comparison of chemical shifts and changes of relaxation parameters caused by coordinate covalent bond formation;
2. Infrared spectroscopy, through comparison of the stretching of bonds or shifting of absorption caused by coordinate covalent bond formation;
3. Mass spectrometry;
4. Molar conductivity or magnetic measurements; and
5. X-ray crystallography.

The key premise to this invention is that two or more biologically active agents are bound together in such a fashion to approximate the kind of covalency inherent in carbon-heteroatom bonds. It is an embodiment of this invention that this kind of covalency can best be achieved using metal coordination chemistry. It is a further embodiment of this invention that the bond between the metal and the respective biologically active agent is labile enough that it would break once the entire hetero-ligated metal coordination complex comes in contact with another biologically relevant entity such as a receptor for the biologically active agent.

Once this first bond between the biologically active agent and the metal is broken, the second biologically active agent that is also bound to the same metal is now available to bind to its receptor at a location that is kinetically synergistic to the first biologically active agent's binding to its receptor.

It is a critical component of this invention that the two biologically active agents act on their respective receptors in such a manner that the biological effect of the two events are synergistically linked to maximize the response at the receptor, thus minimizing the requirement by the receptor for the biologically active agent.

In a most preferred embodiment of the invention this synergy is imparted by coordinating both biologically active agents to a metal, such that a new composition of matter consisting of the two biologically active agents and the metal is formed.

Synthesis of compound libraries as part of a drug discovery process in combinatorial chemistry has "taken its place as a synthetic tool, complementary to rational design, with the power to identify compounds with beneficial biological, catalytic, binding, sensing, and material properties". (M. Krier et al., Design of Small-sized Libraries by Combinatorial Assembly of Linkers and Functional Groups to a Given Scaffold Application to the Structure-based Optimization of Phosphodiesterase 4 Inhibitor, J Med Chem 2005, 48 (11), 3816-22). This method can quickly lead to large numbers of molecules. For example, a molecule with three points of diversity ($R_1$, $R_2$, and $R_3$) can generate $N_{R1} \times N_{R2} \times N_{R3}$ possible structures, where $N_{R1}$, $N_{R2}$, and $N_{R3}$ are the number of different substituents utilized. Infinite variations on a core template are theoretically possible, making these libraries difficult to screen and often difficult to synthesize. In order to gain the maximum amount of information from the minimum number of experiments the current practice of rational combinatorial chemistry requires the optimization of screening libraries, i.e. a minimal size with maximal chemical diversity. To limit the magnitude of library size to 10**2, computational chemists have developed algorithms to select a representative subset. "Virtual libraries are assessed by techniques including Monte Carlo calculations, genetic algorithms, artificial neutral network, or simply statistical sampling with user-defined property ranges."

Traditional combinatorial methods involve assembly of user-selected building blocks composed of a scaffold, attached to a linker, modified by a functional group. From a medicinal chemistry point of view, these libraries are usually generated on the basis of known pharmacophores as scaffolds. We have developed a rational combinatorial chemistry program for the discovery of metal coordinated pharmaceuticals.

Our approach is an adaptation where we utilize known pharmaceuticals as scaffolds, and metal ions as linkers. The functional group is selected from a class of FMDD ligands capable of bonding to the metal, such as, but not limited to, amino acids, lipids, carbohydrates, nucleic acids, peptides, and bioadhesives, and chosen to improve PK properties. This approach offers a number of advantages, including:
1) Development of a practical synthetic methodology based on coordination chemistry which can be applied to a combinatorial program;
2) In contrast to most combinatorial programs, our linker is not a passive participant, but is responsible in large part for the improved pharmacokinetic properties of these molecules;
3) Each molecule can be considered as a tool to probe the different pharmacokinetic properties of the modified drug deriving from the metal/FMDD ligand combination;
4) Utilizing a subset of about 10 metals, and 20 FMDD ligands (for the case of amino acids), the criteria of small-sized libraries associated with each known trade drug is met. We believe certain motifs of pharmacokinetically beneficial metal/FMDD ligand combinations will arise allowing for further reduction in library size when applied to compounds generated from different drug scaffolds.

The mechanism by which kinetic synergy potentiates the pharmacologic effect of biologically active agents can be explained in a variety of ways and depends on the disease state in question. The following sections explain this concept as it applies to CNS disorders, cancer, cardiovascular diseases, inflammatory bowel diseases, pain and other disease states.

Use in Pain Management

The sensation of pain results from intense or high frequency stimulation, or potentially tissue damaging stimuli acting on cutaneous receptors called nociceptors. Nociceptors respond to pressure, heat, cold and chemicals and their activation is modulated by the strength of the stimulus.

Sensation of stimuli, pain or touch, is transmitted from the peripheral sensory neurons to the afferent neurons, grouped into the excitatory, the sensitizing and the inhibitory. Stimuli resulting from tissue damage produce an inflammatory array that acts on these groups of receptors in varying degrees, depending on the stimulus. Onward transmission of these signals to the CNS depends on the balance of inputs to and from the dorsal horn neurone in the spinal cord, all of which are regulated by a complex array of neurotransmitter receptors and voltage-gated ion channels (potassium, sodium and calcium).

Hyperalgesia, repeated noxious stimulus, and allodynia, non-noxious stimulus that is perceived as pain, are initiated as peripheral sensitization of nociceptors leading to central sensitization where spinal processing of the afferent inputs propagates the original pain signal. These central sensitization pre-synaptic neurons propagate and amplify the pain nociception by releasing neurotransmitters; the two more important of these include substance P acting on the neurokinin-1 (NK-1) receptor and glutamate acting on the N-methyl-D-aspartate receptor (NMDA-R). Efforts to develop analgesics acting on the NK-1 receptor have been unsuccessful, thus analgesic agents that act on the NMDA receptor have become important for the relief of hyperalgesia due to chronic or neuropathic pain.

First order neurons terminate in the dorsal horn of the spinal cord where the electrochemical impulse opens voltage-gated calcium channels in the presynaptic bouton. The resultant influx of calcium releases glutamate into the synaptic space, which acts via the Alpha-amino-3-hydroxy-5-methyl-4-isoxazolepropionic acid receptor (AMPA-R) to produce a rapid excitatory post-synaptic potential. Repeated stimulation of AMPA receptors releases peptides, which causes depolarization of the receptor membrane relieving the Mg block from the pore of the NMDA receptor. Released glutamate can now bind to and activate the NMDA-R on the second order neuron leading to a hyper-excitable state (i.e. transmission of pain signal). This signal will continue until the stimulus stops or the NMDA receptor is blocked.

Transmission of pain can be suppressed in the dorsal horn at the pre-synaptic level or post-synaptically on the dorsal horn neurone. Preventing depolarization of key receptors in the dorsal horn (e.g. glutamate receptors) can prevent pain and brain tissue damage. The NMDA receptor is a powerful switch for central sensitization and turning that receptor off will block the hyperexcitability cascade and impart an analgesic effect. Regulation of expression of NMDA and AMPA receptors may also have an impact on the excitatory condition. The NMDA receptor is divided into subunits that are binding sites for glutamate, glycine, magnesium, zinc and phenylglycidine.

Figure 2:
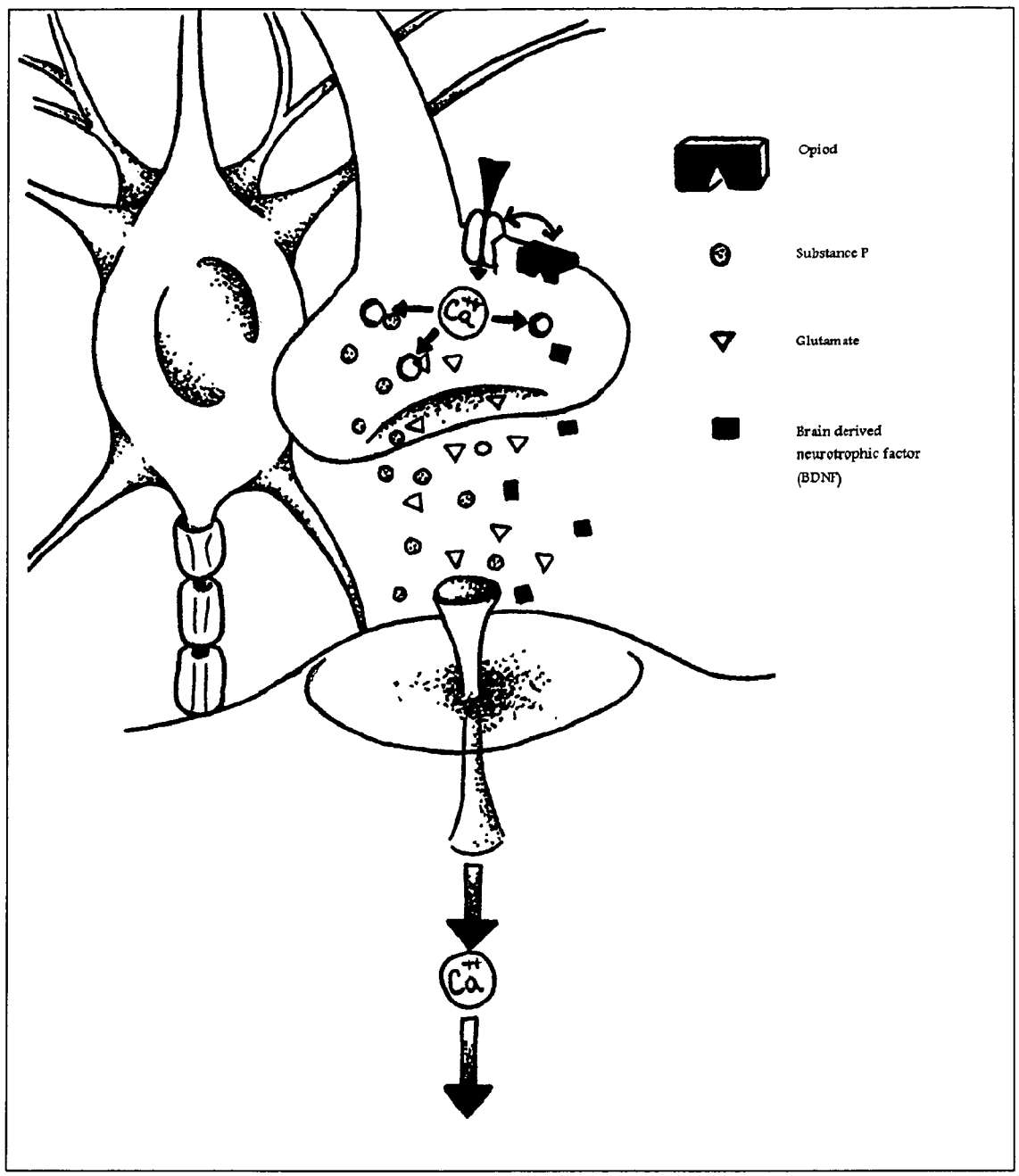
FIG. 2 illustrates a low dose opioid binding to its receptor generating a signal to release less neurotransmitter, which in turn, reduces the intensity of the propagation signal.

Another important method of blocking pain involves the use of opioid receptor agonists. The opioid system comprises the μ-opioid receptor (MOP), δ-opioid receptor (DOP) and the κ-opioid receptor (KOP), each of which have an associated cognate ligand, opiomelanocortin, enkephalin and dynorphin, respectively. Opioid receptors are expressed on the terminals of 1° afferent neurons (FIG. 1) and on the dendrites of post-synaptic neurons. MOP has the widest distribution in the CNS, and is thus the most important opioid receptor for pain management. Activation of the opioid receptor leads to inhibition of the voltage-gated (voltage-dependant) calcium channels, as shown in FIG. 2, and stimulation of potassium efflux. (M. Stillman, Clinical Approach to Patients With Neuropathic Pain, Cleve. Clin. J. Med., 2006, 73 (8), 726-739).

Perception of pain involves a complex array of networks from the viscera, skin and muscle to the spinal cord to the brain and back again. This integrated feedback of pain perception within the neuron involves dynamic control of neurotransmitter release that is highly regulated (dynamic distribution ensemble). (A. J. Holdcroft, Core Topics in Pain, Cambridge University Press: United Kingdom, 2005). The crosstalk between the different receptors on a particular neuron has been documented with respect to opioid receptors and Ca channels. (H. Buschmann et al., Analgesics: From Chemistry and Pharmacology to Clinical Application, Wiley-VCH: Federal Republic of Germany, 2002). Cross talk between the different opioid receptors is further evidenced by dcx-receptor being complexed with m-receptors and that sub-antinociceptive doses of [D-Pen$^2$,D-Pen$^5$]enkephalin (DPDPE) potentiated m-receptor-mediated analgesia. At higher doses DPDPE acted as an agonist at the dncx-receptor and induced analgesia. (A. Corbett et al., Opioid Receptors, http://opioids.com/receptors/index.html).

There is evidence to suggest that voltage dependant calcium channels are a critical component of development of opioid tolerance and dependence. MOP, DOP and KOP mediate the calcium channels and blocking them with opioids will dampen the first order electrochemical impulse. Opioid dosage can be reduced without affecting analgesia by co-administering a Ca channel blocker. (Buschmann, Id.) Thus, the activity and contribution to transmission or blocking of pain signals from Ca channels and opioid receptors, particularly MOP, is dependant on the relative kinetics of each part of the neuron.

Since Ca channels and opioid receptors are interrelated kinetically, it stands to reason that this type of kinetically dependant cross talk would occur intersynaptically, as well as intrasynaptically. Indeed, it has been proposed that combining a Ca channel blocker with a MOP agonist in a single molecule would have excellent pharmacologic properties. (Buschmann, Id) In addition, this cross talk has been shown to be advantageous in reducing tolerance and dependence by combining a MOP agonist with a DOP antagonist. (S. Ananthan, Opioid Ligands with Mixed Mu/delta Opioid Receptor Interactions: An Emerging Approach to Novel Analgesics, AAPS J, 2006, 8 (1), E118-25). MOP, DOP and KOP have high density of these receptors in the dorsal horn (DH), where modulation of N-methyl-D-aspartic acid (NMDA) receptor activation occurs. (Holdcroft, Id.). It is apparent that the dynamic distribution ensemble is a very critical component of pain signaling in the DH; central sensitization, therefore, is that part of pain management where synergy between different methods of analgesia can best be enhanced. This is supported by evidence that suggests that sensitization can only be partly explained by the changes in the periphery and that hyperalgesia and allodynia after injury has a central component. (A. B. Petrenko et al., The Role of N-methyl-D-aspartate (NMDA) Receptors in Pain: A Review, Anesth Analg, 2003, 97 (4), 1108-16).

Acute morphine administration has been shown to have a variety of profound effects on many other neurotransmitters; this group comprises fast-acting neurotransmitters including excitatory amino acids such as glutamate and slower-acting neurotransmitters such as norepinephrine, epinephrine and serotonin, as well as, dopamine and a variety of neuropeptides.

The state of activity of opioid receptors is a complex interaction depending upon interactions with other intracellular mediators. For example, calcium calmodulin-dependant protein kinase II (CaMKII) mediates postsynaptic signaling by NMDAR. CaMKII is preferentially located in pain-processing centers in the CNS, particularly the dorsal horn. Another mediator, PKC, may mediate $Ca^{2+}$-dependant inactivation of NMDA receptor. The mediation by CaMKII contributes to the simultaneous blocking of MOP and NMDA-R, which reduces the threshold amount of glutamate released. This, in turn, reduces the amount of NMDA-R antagonist required. In addition, blocking of the NMDA-R signal dampens the overall nociception making the opioid more effective. Since mediators are influenced by kinetic factors, potentiation depends on the relative kinetics of receptor blocking and activation, particularly activation of MOP.

Pain therapeutic targets include inflammation reduction, ion channel blocking and signaling pathway modulation. Treatment of pain deriving from the dynamic distribution ensemble view warrants multiple therapeutic interventions, incorporating one of the therapeutic targets or combinations thereof. For example, intrathecal magnesium extended the duration of fentanyl analgesia. (A. Buvanendran et al., Intrathecal Magnesium Prolongs Fentanyl Analgesia: A Prospective, Randomized, Controlled Trial, Anesth Analg, 2002, 95 (3), 661-6). As another example, morphine anti-nociception was potentiated by pentobarbital. (R. M. Craft & M. D. Leitl, Potentiation of Morphine Antinociception by Pentobarbital in Female vs. Male Rats, Pain, 2006, 121 (1-2), 115-25). Third, activation of phsopholipase-A2 (PLA2) is linked to activation of voltage-sensitive potassium conductance, which explains the synergy between opioids and NSAID's (Corbett, Id.).

Interestingly, there are limitations to opioid potentiation methods. For example, the non-steroidal anti-inflammatory drug (NSAID), ibuprofen, potentiates hydrocodone and oxycodone but not morphine or fentanyl. Similar limitations have been observed with NMDA-R antagonists as well, where ketamine affected long term potentiation in combination with fentanyl but only if it is administered with fentanyl and prior to nociception in perioperative procedures. Conversely, dextromorphan and memantine failed in clinical trials as adjunct therapy with opioid analgesics. In addition, tetrahydrocannabinol and the opioid receptor agonist, piritramide, do not act synergistically in post operative pain.

NMDA-R antagonists, voltage-gated ion channel blockers and NSAID's, which include COX-2 inhibitors, are the most studied adjunct therapeutic classes. (J. A. Kemp & R. M. McKernan, NMDA Receptor Pathways as Drug Targets, Nat. Neurosci., 2002, 5 Suppl, 1039-42; A. R. Campos et al., Ketamine-induced Potentiation of Morphine Analgesia in Rat Tail-flick Test: Role of Opioid-, Alpha2-adrenoceptors and ATP-sensitive Potassium Channels, Biol. Pharm. Bull., 2006, 29 (1), 86-9; C. R. Lin et al., Antinociceptive Potentiation and Attenuation of Tolerance by Intrathecal Electric Stimulation in Rats, Anesth. Analg., 2003, 96 (6), 1711-6; T. J. Schnitzer, Pain Management Today—Optimising the Benefit/risk Ratio: Defining the Role of Weak Opioids and Combination Analgesics, Clin. Rheumatol., 2006, 25 Suppl 1, S1; J. S. Kroin et al., Cyclooxygenase-2 Inhibition Potentiates Morphine Antinociception at the Spinal Level in a Postoperative Pain Model, Reg. Anesth. Pain Med., 2002, 27 (5), 451-5). Yet there are other approaches to pain therapy that may also be used as adjunct therapies with opioid analgesics, which include 1) acetylcholine receptor agonists, 2) adenosine neurotransmitters, 3) P2 receptor antagonists, 4) cannabinoids, 5) vanilloids and the VR1 receptor agonists, 6) substance P and the NK receptor antagonists, 7) $CGRP_1$-receptor antagonists, 8) nitric oxide, 9) antidepressants, 10) anticonvulsants, 11) alpha-2 adrenergic agonists and 12) GABA agonists. (Holdcroft, Id.; Buschmann, Id.; J. F. Wilson, The Pain Divide Between Men and Women, Ann. Intern. Med., 2006, 144 (6), 461-4; P. Lyden & N. G. Wahlgren, Mechanisms of Action of Neuroprotectants in Stroke, J. Stroke Cerebrovasc. Dis., 2000, 9 (6 Pt 2), 9-14; J. S. Kroin et al., Clonidine Prolongation of Lidocaine Analgesia After Sciatic Nerve Block in Rats is Mediated Via the Hyperpolarization-activated Cation Current, Not by Alpha-adrenoreceptors, Anesthesiology, 2004, 101 (2), 488-94.)

Pharmacokinetics is a critical component of the efficacy of any drug. Some of the limitations associated with synergistic application of analgesic reagents could very well be due to the relative pharmacokinetics of the respective analgesic agents. Certainly the dynamic distribution ensemble view and the importance of cross talk between neurotransmitters and receptors support this premise. It is an embodiment of this invention, therefore, that by pharmacokinetically controlling the administration of receptor antagonists, neurotransmitters, receptor agonists, or anti-inflammatory agents relative to opioid analgesics, that maximum synergy between the two component analgesics will be accomplished. It is a further embodiment of this invention that this maximum synergy will result in lower dosing required for both components, thus delaying tolerance and perhaps avoiding addiction and side effects associated with the adjunct analgesic.

Opioid tolerance is clearly a heterogeneous syndrome where no one single mechanism or loci is entirely responsible. Down regulation of opioid receptors is believed to be a contributing factor to opioid tolerance. (D. E. Keith et al., Mu-Opioid Receptor Internalization Opiate Drugs Have Differential Effects on a Conserved Endocytic Mechanism in Vitro and in the Mammalian Brain, Mol. Pharmacol., 1998, 53 (3), 377-84). Up-regulation of the entire cAMP pathway in the locus ceruleus, which is believed to be the primary site for opioid physical dependence, may also contribute to tolerance. (E. J. Nestler & G. K. Aghajanian, Molecular and Cellular Basis of Addiction, Science, 1997, 278 (5335), 58-63). Multiple other neurotransmitter systems have been implicated in opioid tolerance. Rebound adenylyl cyclase activity in withdrawal may be a fundamental step in eliciting the withdrawal behavior. (H. O. Collier et al., Quasi Morphine-abstinence Syndrome, Nature, 1974, 249 (456), 471-3). Combining analgesia with antagonists has been proposed to reduce tolerance. One could add a small amount of a potent analgesic, such as etorphine, with an antagonist to provide analgesia without tolerance. (Corbett, Id.) Chronic administration of opioid antagonists, primarily naltrexone, will cause a significant up-regulation or increase in density of MOP. (E. M. Unterwald et al., Quantitative Immunolocalization of Mu Opioid Receptors Regulation by Naltrexone, Neuroscience, 1998, 85 (3), 897-905).

Opiates appear to enhance dopaminergic tone and through that enhancement achieve some, most, or all of their reinforcing or rewarding effects. Cocaine caused a striking increase in extracellular dopamine concentrations in the nucleus accumbens, and moreover the combination of cocaine and heroin caused a synergistic elevation. (S. E. Hemby et al., Synergistic Elevations in Nucleus Accumbens Extracellular Dopamine Concentrations During Self-administration of Cocaine/heroin Combinations (Speedball) in Rats, J. Pharmacol. Exp. Ther., 1999, 288 (1), 274-80). Acute and chronic morphine administration increases neuroplasticity, which is mediated in part though action of dopamine D1 receptors. (M. J. Kreek, Molecular and Cellular Neurobiology and Pathophysiology of Opiate Addicition, Neuropsychopharmacology: The fifth Generation of Progress, 2002, 1491-1506). Interfering with the rapid changes in the dopaminergic tone, perhaps with dopamine receptor blocker, may prevent some of the opiate drug dependency.

It is an embodiment of this invention that an FMDD ligand be selected from the group consisting of adjunct therapeutic agents listed above, which include NMDA-R antagonists, voltage-gated ion channel blockers, NSAID's, acetylcholine receptor agonists, adenosine neurotransmitters, P2 receptor antagonists, cannabinoids, vanilloids, VR1 receptor agonists, substance P, NK receptor antagonists, $CGRP_1$-receptor antagonists and nitric oxide. It is a preferred embodiment of this invention that an FMDD ligand be selected from the group consisting of NMDA-R antagonists, voltage-gated ion channel blockers and NSAID's. In a most preferred embodiment of this invention an FMDD ligand is an NMDA-R antagonist.

Infusion with low dose receptor antagonists potentiates analgesia by opioids. Delivering receptor antagonists with opioid concertedly will reduce the dosing requirement for each component and may even obviate the need to infuse the receptor antagonist or the opioid.

The potentiation of receptors that are intrinsically linked occurs through a mechanism that relies on the relative kinetics of the biologically active moieties binding to their respective receptors. (Psychological and Physiological Consequences of Noncompetitive Antagonsim of the NMDA Receptor by Ketamine: http://sulcus.berkeley.edu/mcb/165__001/papers/manuscripts/__819.html). So, when two moieties, such as an analgesic and an adjunct reagent, are introduced into the body, their relative migration rates to their respective target receptors may not be coincident with the cross talk required for potentiation to occur. (G. Sathyan et al., The Effect of Dosing Frequency on the Pharmacokinetics of a Fentanyl HCl Patient-controlled Transdermal System (PCTS), Clin. Pharmacokinet., 2005, 44 Suppl 1, 17-24). Therefore, potentiation through synergistic application of two or more biologically active agents involves a kinetic component that, if not incorporated into the drug design, may reduce or eliminate the effect altogether.

The respective receptors are linked by more than just chemistry; there is a frequency component that facilitates the cross talk between the receptors. Potentiation of the receptors is best achieved if the biologically active moieties reach their respective receptors in a manner that closely matches the kinetics of the cross talk between the receptors. Given that the time course of delivery to the target receptors will likely be different for the two moieties, it is also likely that the timing of the attachment to their receptors will not match the frequency of the cross talk. Delivery of the two moieties as ligands in a single molecular entity is a viable method to modulate the frequency of drug delivery.

Figure 3:
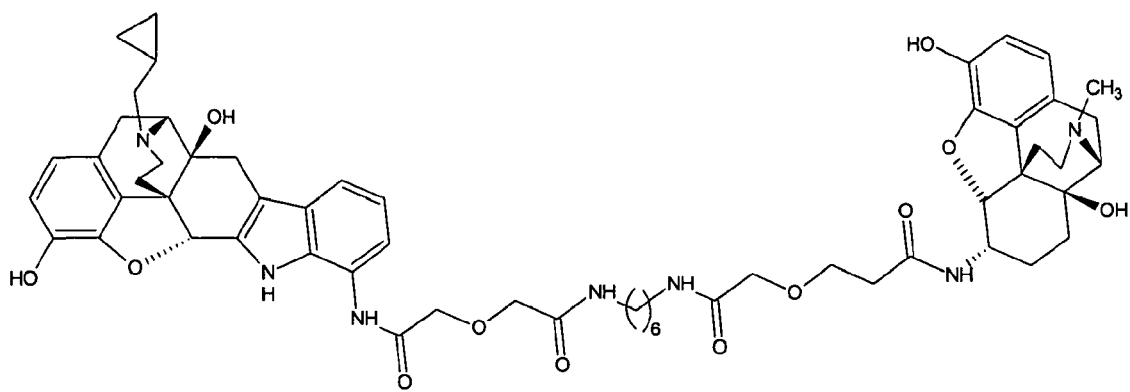
FIG. 3 shows the DOP antagonist, 7'-aminonaltrindole, and the MOP agonist, oxymorphamine, linked with a hexyl-diamine glycolate spacer.

For example, when the DOP antagonist, 7'-aminonaltrindole, and the MOP agonist, oxymorphamine, were linked with a hexyldiamine glycolate spacer (FIG. 3) it was found to be more potent than morphine and to produce no tolerance or physical dependence. (Ananthan, Id.) It is an embodiment of this invention that the synergy between two analgesic agents is maximized when combined in a single molecular entity.

Figure 4:
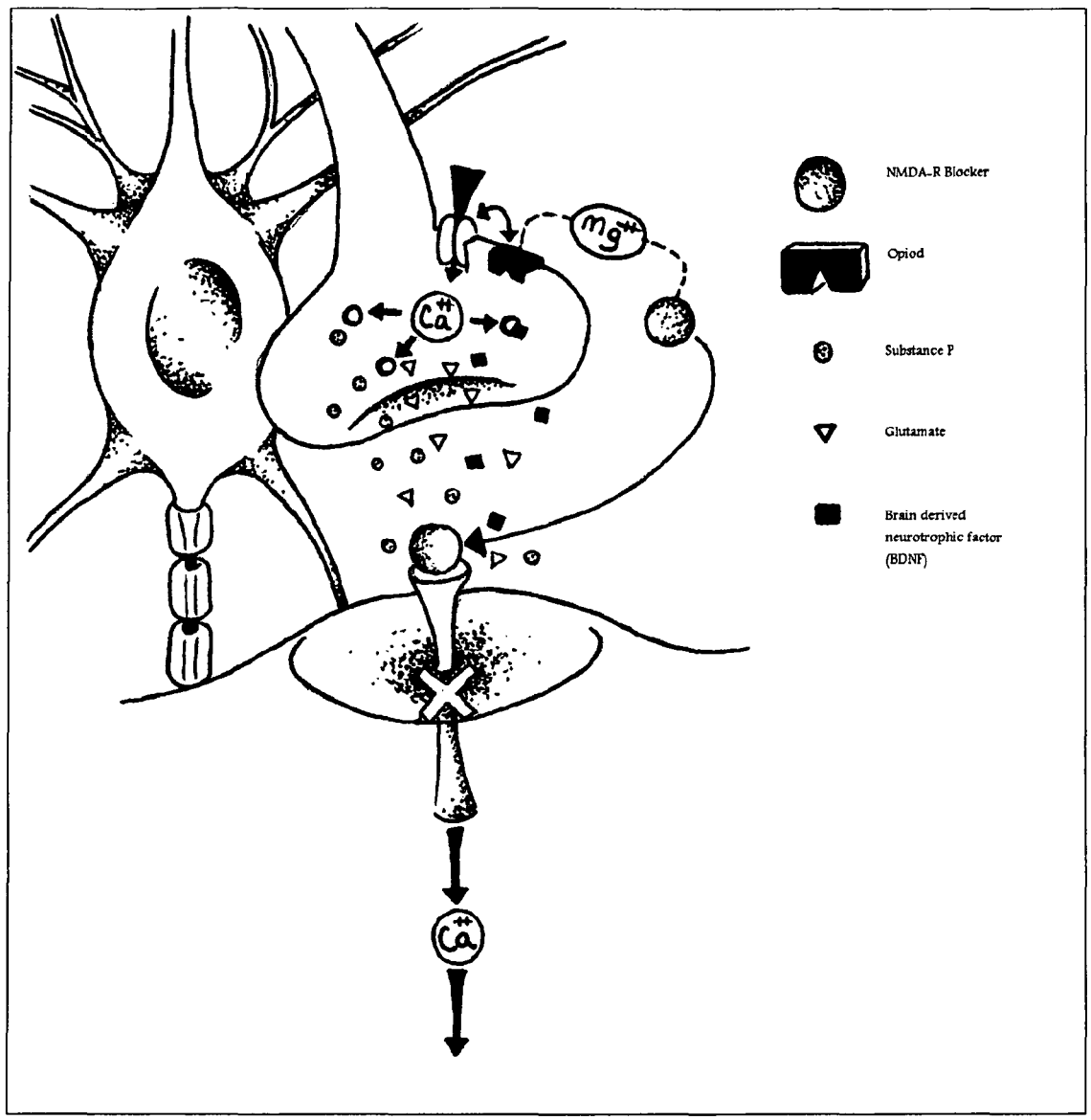
FIG. 4 shows that with FMDD, the low dose opioid of the magnesium complex slows release of the neurotransmitters similar to that shown in FIG. 2, but the residual glutamate is blocked by the NMDA-R antagonist released from the magnesium complex (the ligand-magnesium bond breaking is designated by the dashed lines). Thus both the opioid and the NMDA-R antagonist potentiate the effects of each other in a manner that kinetically approximates the mechanism of pain signal propagation.
Figure 5:
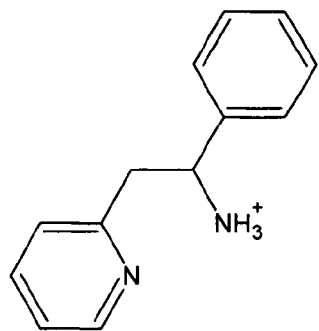
FIG. 5 shows the chemical structure for ARL 15896AR.
Figure 6:
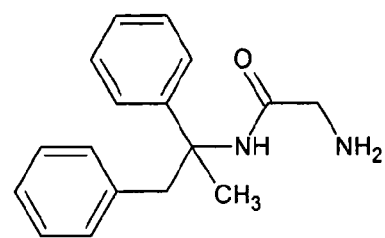
FIG. 6 shows the chemical structure for remacemide.
Figure 7:
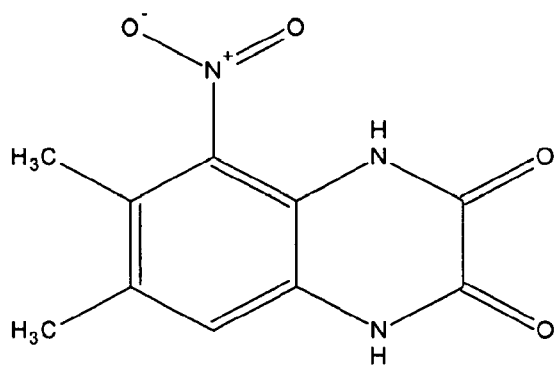
FIG. 7 shows the chemical structure for ACEA1328.
Figure 8:
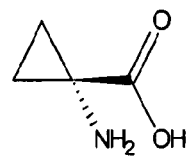
FIG. 8 shows the chemical structure for ACPC.
Figure 9:
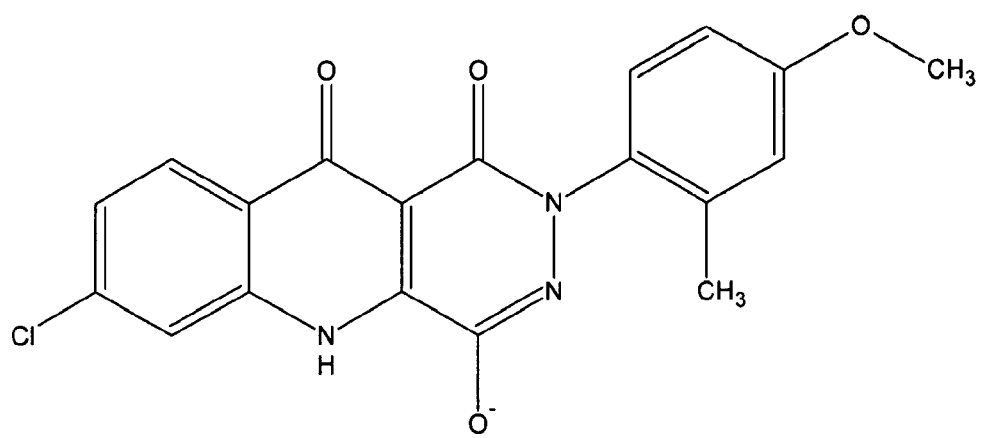
FIG. 9 shows the chemical structure for ZD9379.
Figure 10:
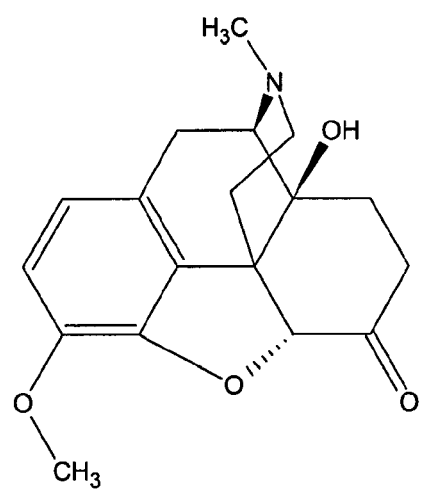
FIG. 10 shows the chemical structure of oxycodone.
Figure 11:
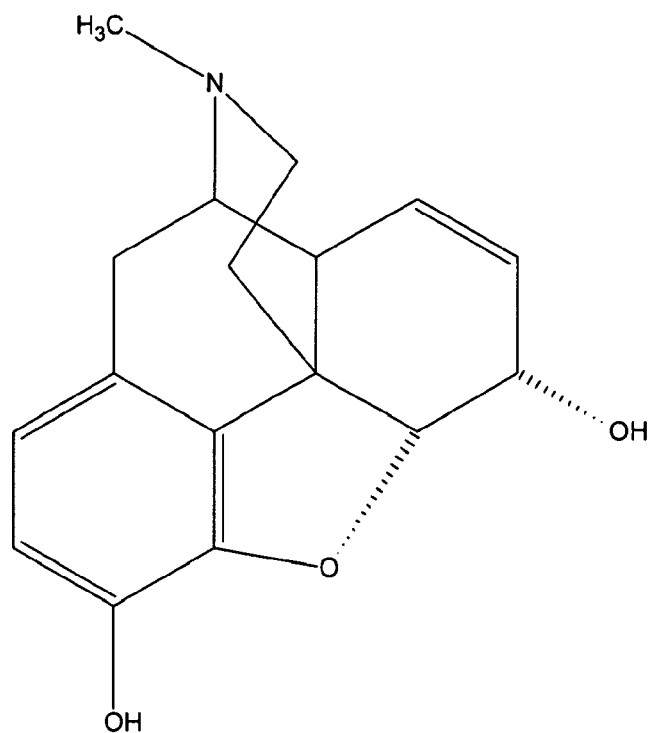
FIG. 11 shows the chemical structure of morphine.

In the above example the length of the linker was critical and, therefore, it may be difficult to optimize potentiation because of the trial and error associated with linker chain length. Metal coordination represents a viable alternative. The two ligands are still part of the same molecule and the complex is designed such that it is stable in the body until another biological entity strips one of the ligands away from the complex. The receptor for the stripped-away ligand could be that entity. The metal:ligand complex that is still intact is then available for binding to the other receptor with or without the metal involved (FIG. 4). The migration distance between the receptors is much shorter than the migration distance from the point of administration to the receptors and, therefore, frequency modulation of drug delivery will more likely match the frequency of the cross talk when the biologically active moieties co-exist as ligands in a single molecular entity and especially when the single molecular entity is bound together as a metal coordinated complex.

In a preferred embodiment of this invention two analgesic agents are selected from the group of NMDA-R antagonists and MOP. Due to specific limitations, in a most preferred embodiment of this invention, ketamine and fentanyl will affect long term potentiation if administered as a single molecular entity.

In certain instances delivering the opioid agonist and an NMDA-R antagonist as a single molecular entity may prevent the interaction of the neurotransmitter with the respective receptor. Many of the analgesic agents mentioned in this document have metal binding capacity. Addition of other stabilizing ingredients or components to the analgesic-metal complex will serve to stabilize the entire complex further. The FMDD complex is designed such that it should be stable enough to survive in the body until it reaches its target organ. If an FMDD ligand is one of the adjunct analgesics discussed earlier, then its role would be to enhance the effect of the analgesic, particularly one of the opioids, as well as stabilize the complex. The complex stability is compromised only when another ligand in the body displaces one or the other analgesic ligands attached to the metal. A receptor for one or the other analgesic ligands will provide the thermodynamic impetus to dissociate the complex. Once the complex is broken down by the receptor, the other analgesic reagent is then free to migrate to its respective receptor. Thus the FMDD potentiation cycle is complete.

Many receptor-evoked cellular responses are known, some of which are involved in mediating the action of other receptors (e.g., inhibition of adenylyl cyclase is linked to tolerance and potentiation of NMDA currents), and examination of these cellular functions may assist in an FMDD analgesic. K-agonists may also be useful in FMDD, such as 6,7-benzomorphans, since they bind to other opioid receptors but show preference for the k-receptor. A new class of opioid agonists based on enkephalin-mimics, in which a lead compound is actually the 6,7-indole analogue of naltrexone, naltrindole, may also provide some useful compounds for FMDD (Corbett, Id.).

In addition to the three well-defined classical opioid receptors, DOP, MOP and KOP, an orphan receptor, ORL-1, has been described, as well. The ORL-1 receptor also has selective agonists, antagonists of it are not well known and therefore designing a drug that binds to both the ORL-1 receptor and the m- or d- receptor may provide analgesic potentiation without causing tolerance or dependence.

Based on the stability and the dissociation mechanism of an FMDD ligand:metal:opioid complex, it is an embodiment of this invention that the complex provides enhanced analgesic effect as a single molecular entity, thereby delivering both analgesics in a pharmacokinetically synergistic manner. It is a further embodiment of this invention that by delivering the analgesic agents as a single molecular entity that enhanced synergy between the reagents is achieved in accordance with the dynamic distribution ensemble view. Furthermore, the enhanced analgesic effect will reduce the dosage required from the opioid and thus reduce tolerance and dependency. In a preferred embodiment of the invention an FMDD ligand analgesic is an NMDA receptor antagonist. Since magnesium is involved in the pathway leading to the hyperexcitable state and that addition of magnesium can mimic the effects of NMDA receptor antagonists it is a preferred embodiment of the invention that the metal used to complex the analgesic agents be magnesium. (S. Begon et al., Magnesium Increases Morphine Analgesic Effect in Different Experimental Models of Pain, Anesthesiology, 2002, 96 (3), 627-32).

It is preferable that the FMDD ligand have metal chelating properties, which in addition to forming a strong bond with the metal can also have the capacity to stabilize the opioid-metal complex in accordance to the principals outlined earlier. The agents that make the best candidates for complexing with magnesium and calcium are those that have a proton on a heteroatom (i.e., oxygen, nitrogen or sulfur) with a $pK_a$ slightly greater than water or less and have an additional heteroatom in close proximity to the first protonated heteroatom such that it can participate in the bonding, or otherwise chelate, with the metal. Compounds that have this arrangement of functional groups are most likely going to bond with a metal, where the resultant metal coordinated active agent will be stable enough in a biological system and survive hydrolysis therein until the complex reaches the target site. In this way, the FMDD ligand and the opioid analgesic will be delivered to the target receptor sites concurrently where the complex will dissociate and each reagent will than impart its respective pharmacologic response. Because the responses are kinetically linked, the synergistic analgesia, with the attendant reduction in tolerance and dependency, is optimized.

Figure 12:
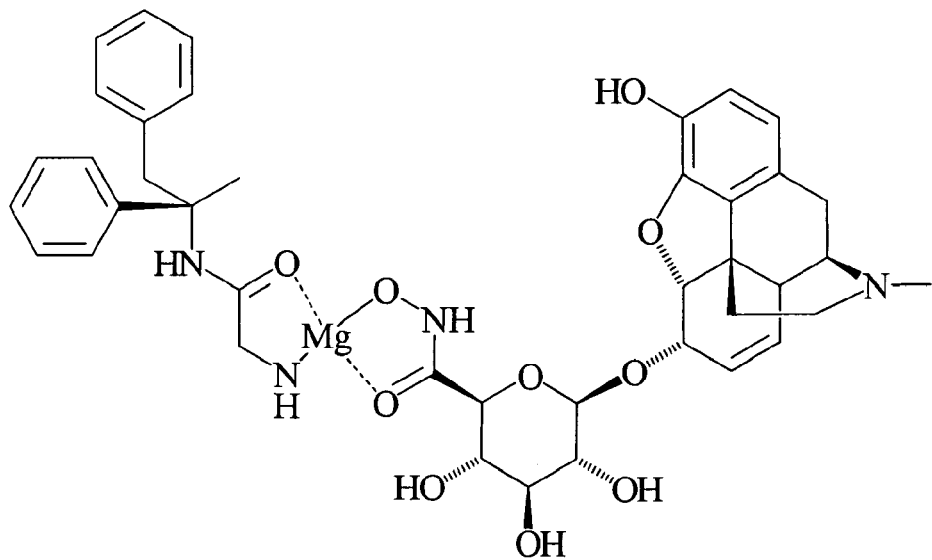
FIG. 12 shows the chemical structure of remacemide:Mg: M6 GHA.

Several NMDA receptor antagonists in varying stages of development, such as ARL 15896AR and remacemide, meet the chelating criteria. Many of the glycine site antagonists undergoing preclinical evaluation, including ACPC, ACEA1328 and ZD9379, are good chelators as well. (C. G. Parsons, NMDA Receptors as Targets for Drug Action in Neuropathic Pain, Eur. J. Pharmacol., 2001, 429 (1-3), 71-8). The opioid narcotic is selected from the group consisting of morphine, morphine-6-glucuronide (M6G), oxymorphone, oxycodone, hydromorphone, codeine and hydrocodone. Amongst the opioid narcotics in the selected group, perhaps the molecular structure of morphine-6-glucuronide (M6G) is best suited for complexation with a metal. Therefore, it is a preferred embodiment of the invention that the complex is ARL15896AR:magnesium:M6G. Hydroxamic acids have shown remarkable stability as metal complexes and, therefore, it is an embodiment of this invention that an opioid analgesic be selected from a group of morphine-6-glucuronide hydroxamic acid (M6 GHA), the metal coordinated analogs and FMDD analogs. Therefore, it is a preferred embodiment of the invention that the complex is ARL15896AR:magnesium:M6 GHA. A most preferred embodiment of the invention is remacemide:magnesium:M6 GHA complex shown in FIG. 12.

In a typical application, the metal complex is formulated for administration and delivered orally or intrathecally. The analgesic effect will have the usual pharmacokinetics, except the dosing is expected to be less than with an opioid alone. The closer to the target site the complex can be delivered the better the probability that the complex will be stable until reaching the target site. Therefore, in a preferred embodiment of the invention FMDD ligand:metal:opioid complex is infused intrathecally.

Use in Treatment of Migraine Headaches

Migraine is a neurological disorder characterized by episodes of often severe, usually one-sided, frequently throbbing or pounding pain, associated with other features, such as nausea or vomiting, sensitivity to body movement, sensitivity to light, or sensitivity to sound, Triptans, 5-$HT_{1B/1D}$ agonists that target the trigeminovascular system and include marketed products such as sumatriptan, rizatriptan and zolmitriptan, are well established agents in treating the pain associated with migraines. 5HT receptors are one of the post-synaptic dorsal horn projection neurons and 5HT (aka serotonin) is one key neurotransmitter responsible for pain modulation at each level throughout the entire body. Serotonin also causes extravasation of plasma proteins and hyperalgesia. Subtype 5HT receptors are localized to nociceptors and mediate peripheral effect of serotonin during inflammation. The triptan molecules effectively block the serotonin-mediated synaptic transmission between the nociceptor and the central neuron in the dorsal horn.

Treximet is a combination of sumatriptan with the NSAID, naproxen sodium, and provides support to the premise that combining two medications can provide more effective relief of pain than using either drug alone. Although the reasons for this have not been made clear by the innovators of Treximet, it is likely due to potentiation of the two drugs. It is therefore an embodiment of this invention that a triptan's and an NSAID's potentiating effect can be optimized if the two drugs are delivered to the respective targeted sites synergistically. It is a further embodiment of this invention that delivering the two drugs as a metal coordination complex is a very effective way to optimize this potentiation. In a preferred embodiment of this invention, the triptan in the metal coordination complex is sumatriptan and the NSAID is naproxen. Since magnesium also possesses anti-migraine properties, a most preferred embodiment of this invention is (sumatriptan)(naproxen)magnesium. It can therefore be demonstrated that in some applications the chelating metal itself may actually play a role in the pharmacodynamics of the FMDD complex.

Krymchantowski, et. al. have reviewed the most current thinking on the future of the treatment of headaches and many of the same adjunct therapies with opioid analgesics have also been implicated as possible modes of action for the treatment of migraines. (A. V. Krymchantowski et al., The Future of Acute Care and Prevention in Headache, Neurol. Sci., 2007, 28 Suppl 2, S166-78). A literature summary of alternative methods of treating headaches and migraines include:

1) Topiramate influences the action of some types of voltage-gated sodium and calcium channels, $GABA_A$ receptors the AMPA/kainate subtype glutamate receptors.
2) Tiagabine inhibits neuronal and glial uptake of GABA
3) Zonisamide blocks voltage-dependant sodium channels, reduces glutamate-mediated exicitatory neurotransmission, inhibits excessive nitric oxide production, scavenges hydroxyl radicals and inhibits carbonic anhydrase.
4) Carvedilol has antioxidant properties.
5) Tizanidine inhibits the release of norepinephrine in the brainstem.
6) Quetiapine has a high affinity for 5-$HT_2$ receptors.

7) Adenosine neurotransmitters exhibit both chronic and acute analgesic properties
8) Vanilloids and the VR1 receptor agonists, such as capsaicin and civamide, leads to rapid desensitization, loss of sensitivity to heat and chemical stimulation.
9) Substance P, $CGRP_1$-receptor and the NK receptor antagonists block neuronal transmission and inflammation.
10) Calcitonin gene-related peptide (CGRP) is thought to have an important role in the pathophysiology of migraines and is currently a new class of migraine drug in clinical trials (e.g. BIBN 4096 BS).
11) Nitric oxide is released in conjunction with CGRP from nerve terminals triggering the migraine cascade.
12) COX increases nociceptive thresholds and causes tenderness.

Thus it is an embodiment of this invention that any two or more of the agonists or antagonists listed above can be combined as a metal coordination complex such that the biological agents will be delivered to their respective receptors with the kinetic synergy necessary to achieve potentiation of said biological agents in accordance with the principles described in this invention.

Use in Treatment of Neurodegenerative Diseases

Parkinson's Disease

Parkinson disease is characterized by loss of motor function control due to degeneration of the dopaminergic neurons and of other neurons in the monoaminergic family in the midbrain. The most prominent neuronal loss occurs in the substantia nigra, which leads to depletion of dopamine in the striatum causing an imbalance between the dopaminergic and cholinergic systems. The resultant excessive release of the inhibitory neuro-transmitter, gamma aminobutyric acid (GABA), leads to the parkinsonian motor dysfunction that characterizes the disease. (M. Di Napoli et al., Molecular Pathways and Genetic Aspects of Parkinson's Disease: From Bench to Bedside, Expert Rev. Neurother., 2007, 7 (12), 1693-729).

Treatment for the resulting motor dysfunction associated with Parkinson disease typically consists of agents that replace dopamine, mimic dopamine activity, or increase dopamine availability in the central nervous system. (J. Rao, Advances in Treatment of Parkinson Disease, Evolving Concepts in Parkinson Disease Pathophysiology, Diagnosis, and Treatment, 2007, 10-13). Maintaining consistent carbidopa-levodopa plasma levels presents a challenge in the treatment of Parkinson disease and results in periods of "off" times, which may require patients to take multiple doses throughout the day. As the disease progresses, adjunctive therapy or additional carbidopa-levodopa doses to minimize or treat the increases in symptomatic "off" time between levodopa doses is usually required. (M. Tagliati, Carbidopa-Levodopa Oraly Disintegrating Tablets, Evolving Concepts in Parkinson Disease Pathophysiology, Diagnosis, and Treatment, 2007, 7-9). Furthermore, although levodopa provides dramatic relief of PD symptoms, prolonged treatment leads to a variety of adverse motor and cognitive effects. (M. J. Marino et al., Glutamate Receptors and Parkinson's Disease: Opportunities for Intervention, Drugs Aging, 2003, 20 (5), 377-97).

The later stages of idiopathic Parkinson's disease (IPD) are characterized by a decline in response to levodopa and motor complications such as dyskinesias and response fluctuations. (C. E. Clarke et al., T. A., A randomized, Double-blind, Placebo-controlled, Ascending-dose Tolerability and Safety Study of Remacemide as Adjuvant Therapy in Parkinson's Disease with Response Fluctuations, Clin. Neuropharmacol., 2001, 24 (3), 133-8). Throughout the progression of the disease, under chronic conditions of enhanced neuronal susceptibility glutamate's lethal action impacts the efficacy of the dopaminergic drugs. (G. C. Palmer, Neuroprotection by NMDA Receptor Antagonists in a Variety of Neuropathologies, Curr. Drug Targets, 2001, 2 (3), 241-71).

There are a host of neurologic disorders that share the classic symptoms of Parkinson disease. Diagnosis for the disease can sometimes be tricky as shown in Table 2. Progressive supranuclear palsy (PSP) and multiple system atrophies (MSA) are examples of neurodegenerative diseases with parkinsonian features. (A. Nicholas, Pathophysiology and Diagnosis of Parkinson Disease, Evolving Concepts in Parkinson Disease Pathophysiology, Diagnosis, and Treatment, 2007, 1-4).

TABLE 2

Differential Diagnosis of Parkinson Disease

| Common Misdiagnosis | Distinguishing Features |
|---|---|
| Essential tremor | Tremor (action, postural), no response to PD drugs |
| Progressive supranuclear palsy | Supranuclear palsy, upright posture, pseudobulbar affect, early gait instability, numerous falls, dysphagia, rarely responds to PD drugs |
| Multiple system atrophy | Autonomic disturbance, cerebellar signs, relative absence of tremor, early gait instability, dysphagia |
| Corticobasal degeneration | Limb apraxia, cortical sensory abnormalities, early dementia, alien limb, rarely responds to PD drugs |
| Diffuse Lewy body dementia | Early dementia, psychosis, agitation |
| Alzheimer disease | Dementia is the primary symptom |
| Drug-induced parkinsonism | Exposure to dopamine-blocking drugs, relative lack of rest tremor and asymmetry, can be reversible |
| Vascular parkinsonism | History of chronic hypertension, stepwise progression (if any), unilateral, imagine relative absence of tremor |

Figure 13A:
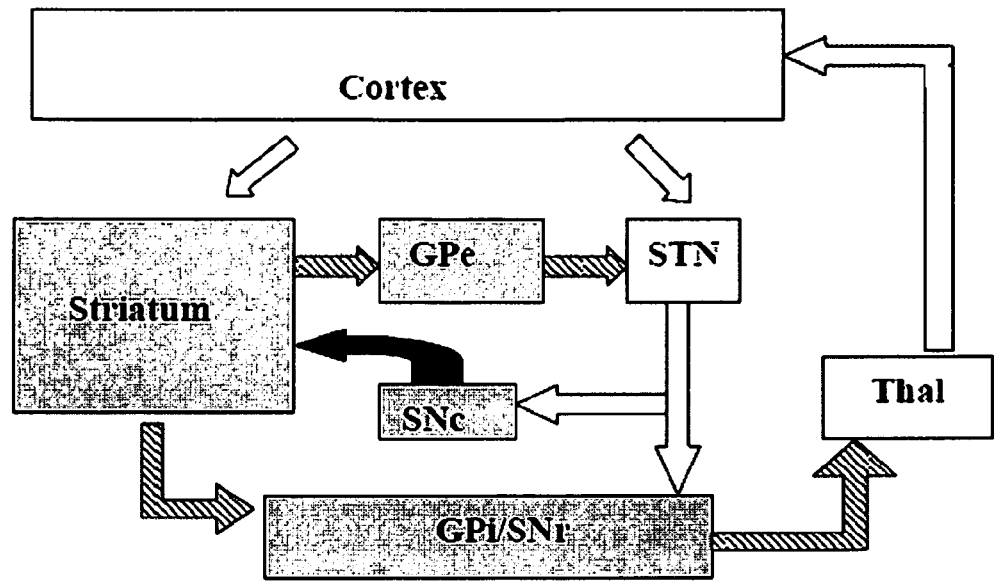
FIGS. 13a and 13b show simplified schematic diagram of the basal ganglia circuit in both the normal and Parkinsonian states. Inhibitory GABAergic projections are indicated by shaded arrows, excitatory glutamatergic projections are indicated by open arrows. A box and black arrow indicates the modulatory dopaminergic nigrostriatal pathway. Note that the loss of dopaminergic modulation of the striatum results in an increase in glutamatergic output from the subthalamic nucleaus to both the basal ganglia output nuclei and the substantia nigra dopamine neurons. GPe=globus pallidus external segment; GPi=globus pallidus internal segment; SNc=substantia nigra pars compacta; SNr=substantia nigra pars reticulata; STN=subthalamic nucleus; Thal=thalamus.

The pathophysiology of Parkinson's disease involves a very complex array of receptors and neurons in the basal ganglia, which are a set of interconnected subcortical nuclei partly responsible for control of motor behavior. (Marino, Id.) The current understanding of the information flow in the basal ganglia is that output from the substantia nigra pars compacta (SNc) is both critical to striatum function and is impacted by a complex set of signals in other components of the circuit. The proper function of the basal ganglia consists of signals that are transferred through its different structures and are typified by inhibitory GABAergic, excitatory glutamatergic and dopaminergic signals. (FIG. 13a).

Figure 13B:
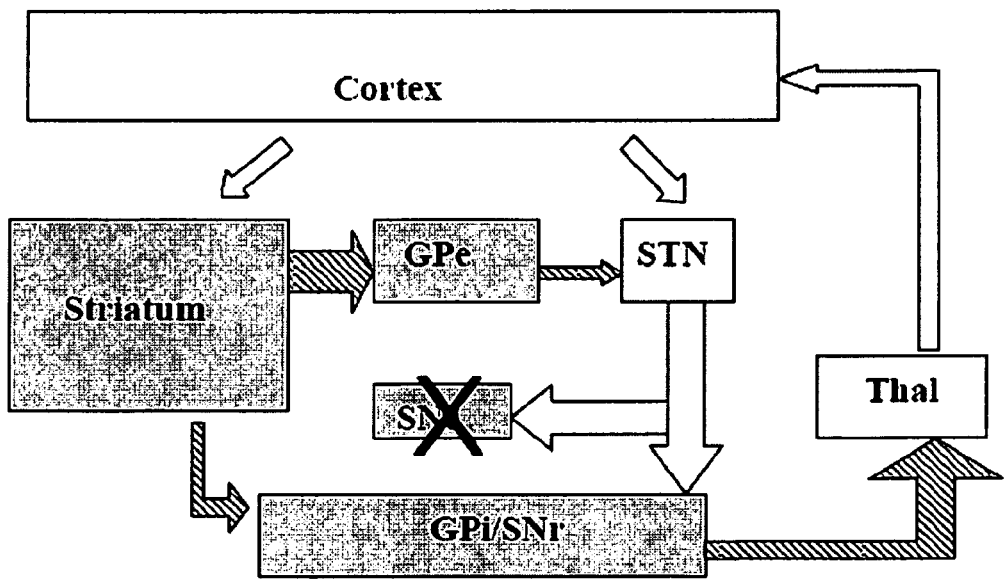

Both the loss of striatal dopamine output and the increased excitatory glutamatergic drive through the indirect pathway are implicated as causative factors in PD patients. (FIG. 13b) These effects create an imbalance between direct inhibition and indirect excitation of the basal ganglia output nuclei, which is crucial for control of normal motor behavior, and alterations in this circuit underlie a variety of movement disorders including PD. (Marino, Id.)

The glutamatergic drive causes glutamate/glycine interactions to release $Mg^{+2}$ from the receptor site into the cytosol, thereby allowing passage of calcium through the ion channel into the cell. This ion channel is further controlled by the NMDA receptor that can trigger calcium influx but only when the ion channel is open. This causes the release of excess amounts of glutamate and the resultant receptor-operated calcium flux into the cell may be of sufficient magnitude as to be lethal to neurons. (Palmer, Id.) The whole pathophysiology of PD is self exacerbating because excessive excitatory drive through the indirect pathway underlies the increase in basal ganglia outflow, which is believed to be responsible for further neurodegeneration of SNc neurons. (Marino, Id.) Further, abnormal accumulation of iron and copper in the brain has been associated with the development of PD and other neurodegenerative disorders.

It is not surprising then that secondary disruptions in the glutamatergic system are responsible for many of the motor symptoms of PD and, therefore, the glutamatergic system has been the focus for providing several potential targets for novel intervention in PD (Marino, Id.).

There are studies that show that the basal ganglia complex have interconnected receptors that crosstalk much in the same way that other CNS receptors do. (Klopman, et. al.) demonstrated the in silico effectiveness of compounds bearing pharmacophores of MAO-B inhibitors, dopamine agonists and NMDA antagonists; theoretically combining these pharmacophores into a single molecular entity could synergistically enhance their antiparkinson effect. (G. Klopman & A. Sedykh, An MCASE Approach to the Search of a Cure for Parkinson's Disease, BMC Pharmacol., 2002, 2, 8). One could envision extrapolating from the pharmacophore combination principals in this paper by performing the same function but retaining the entire integrity of the molecule to ensure optimum pharmacologic effect. Thus it is an embodiment of this invention that pharmacophores on antiparkinson's drug can be combined as a single molecular entity by complexing each of the drugs to a metal.

The NMDA receptor plays a key role in many neurophysiologic functions including neurotransmission through a complex set of modulatory sites located on the NMDA receptor. These functions are integrated with other neurotransmitter systems through a variety of mechanisms involving the modulation of NMDA receptor currents. (Marino, Id.)

Agonist binding to the NMDA receptor allows high calcium ion flux, which contributes to synaptic plasticity, development and degeneration. The NR2B subunit selective and the high and low affinity use-dependent NMDA antagonists exert their dynamic control of calcium entry into the neuron. (Palmer, Id.) A key component to the NMDA receptor's synergistic neurotransmission is the role that magnesium plays in the calcium flux. In the resting state magnesium blocks the ion channel, which imparts a strong voltage dependence to the channel. This allows the NMDA receptor to act as a coincidence detector, which requires participation from glutamate and glycine, and postsynaptic depolarization before conducting current. (J. Z. Tsien, Linking Hebb's Coincidence-detection to Memory Formation, Curr. Opin. Neurobiol., 2000, 10 (2), 266-73; P. H. Seeburg et al., The NMDA Receptor Channel: Molecular Design of a Coincidence Detector, Recent Prog. Horm. Res., 1995, 50, 19-34).

There have been many reports on the complex interactions between the NMDA receptors and the glutamate system in the striatum. For example, intrastriatal injections of both competitive and noncompetitive NMDA antagonists was shown to induce an increase in locomotor behavior that is mediated by a mechanism involving the D1 subtype of dopamine receptors. (M. Morelli et al., Opposite Effects of NMDA Receptor Blockade on Dopaminergic D1- and D2-mediated Behavior in the 6-hydroxydopamine Model of Turning: Relationship with c-fos Expression, J. Pharmacol. Exp. Ther., 1992, 260 (1), 402-8). Examples of D1 subtype receptor agonists of which would potentially be a component of the FMDD complex include the catecholamines (e.g. apomorphine, dihydrexidine, dinapsoline, dinoxyline and dopamine). Yet there are studies that suggest that competitive NMDA receptor antagonists actually increase dyskinesias. It is important to note here that this apparent contradiction in NMDA receptor antagonists activity can be explained by species differences, differences in the extent of the MPTP-induced lesion, and differences in the pharmacokinetic profile of the compounds used (Marino, Id.). Moreover, the NMDA antagonist remacemide has been observed to enhance levodopa's effects in stimulating locomotor activity in reserpinized rats. (J. T. Greenamyre et al., Antiparkinsonian Effects of Remacemide Hydrochloride, a Glutamate Antagonist, in Rodent and Primate Models of Parkinson's Disease, Ann. Neurol., 1994, 35 (6), 655-61; Remacemide Information Summary: http://www.ninds.nih.gov/funding/research/parkinsonsweb/drug_summaries/remacemide.htm). A low dose of remacemide (5 mg/kg) administered with the lowest effective dose of levodopa (75 mg/kg) was able to increase horizontal motor activity significantly (9-fold) over that found with levodopa given alone (2). Other studies also demonstrated the potentiated effects of levodopa in animal models of Parkinson's disease when NMDA antagonists are added. (S. Kaur & M. S. Starr, Differential Effects of Intrastriatal and Intranigral Injections of Glutamate Antagonists on Motor Behaviour in the Reserpine-treated Rat, Neuroscience, 1997, 76 (2), 345-54).

Thus, it is an embodiment of this invention that optimum pharmacologic response of an NMDA receptor antagonist can be attained when its synergistic effect is pharmacokinetically controlled. It is a further embodiment of the invention that this pharmacokinetic control is accomplished by complexing the NMDA receptor antagonist and the dopaminergic drug to a metal.

Given the complex network of neurons, receptors and neurotransmitters in the basal ganglia responsible for motor control it is not surprising to learn that several classes of receptor antagonists have been studied as a treatment for PD and other related disease states. For example dopamine receptor agonists, MAO-B inhibitors and NMDA receptor antagonists are all known to have antiparkinson effects. (S. Isaacson, Current Medical Treatment of Parkinson Disease, Evolving Concepts in Parkinson Disease, Pathophysiology, Diagnosis, and Treatment, 2007, 4-6). In addition studies have demonstrated the benefit of NMDA receptor antagonists in the reducing levodopa-induced dyskineasias (Clarke, Id.).

Other classes of compounds affecting the NMDA receptor, are the subunit-selective antagonists acting at the glycine site, allosteric inhibitors at the polyamine site, and inhibitors of glutamate release (Marino, Id.; M. Ankarcrona et al., Glutamate-induced Neuronal Death: A Succession of Necrosis or Apoptosis Depending on Mitochondrial Function, Neuron., 1995, 15 (4), 961-73; S. A. Lipton, S, Prospects for Clinically Tolerated NMDA Antagonists: Open-channel Blockers and Alternative Redox States of Nitric Oxide, Trends Neurosci., 1993, 16 (12), 527-32; D.C. D'Sousa & John Krystal, Clycine Site Agonists of the NMDA Receptor: A Review, CNS Drug Reviews, 1995, 1 (2), 227-260.) Glutamate acts on two classes of receptors, the ionotropic glutamate receptors (iGluRs) and the metabotropic glutamate receptors (mGluRs). Both the iGluRs and the mGluRs are potential targets for the treatment of PD. It is of interest to note that mGluR5 plays a role in the facilitation of burst firing in the STN and presynaptic mGluRs may play an important role in regulating the excitatory input to the basal ganglia thus mGluRs antagonists may be ideal candidates for FMDD synergy with other drugs to provide antiparkinsonian effects (Marino, Id.).

Multiple studies have found that structurally diverse AMPA antagonists synergize with levodopa or direct dopamine agonists to produce increase turning behavior or reversal of akinesia in 6-OHDA-lesioned rats. The decrease in effectiveness to repetitive levodopa treatments observed in rodent models is completely blocked by combining an AMPA antagonist with levodopa (Marino, Id.).

Other classes of receptor agonists and antagonists that may be suitable candidates for FMDD treatment of PD are kainic acid and metabotropic receptors linked to G-protein actions, anticholinergic agents and adenosine agonists. (C. G. Parsons et al., Glutamate in CNS Disorders as a Target for Drug Development: An Update, Drug News Perspect., 1998, 11 (9), 523-69; A. Napolitano et al., New Directions in Parkinsons Research and Treatment, Expert Opinion on Therapeutic Patents, 1998, 8 (10), 1251-1268).

Perhaps the most well-known NMDA receptor antagonist is remacemide. Remacemide was originally described as a fast sodium channel blocker and has previously been tested in clinical trials for epilepsy, stroke and Alzheimer's disease. (J. A. Kemp & R. M. McKernan, NMDA Receptor Pathways as Drug Targets, Nat. Neurosci., 2002, 5 Suppl, 1039-42; C. Missale et al., The NMDA/D1 Receptor Complex as a New Target in Drug Development, Current Topics in Medicinal Chemistry, 2006, 6, 801-808). There was evidence that remacemide produced an improvement in patients' symptoms, particularly with regard to motor impairment. (Clarke, Id.) Remacemide is a safe and tolerable adjunct to dopaminergic therapy for patients with Parkinson's disease and was found to potentiate the actions of levodopa. (S. Schwid, A Randomized, Controlled Trial of Remacemide for Motor Fluctuations in Parkinson's Disease, Neurology, 2001, 56, 455-462). Work with remacemide in 1-methyl-4-phenyl-1,2,3,6-tetrahydropyridine (MPTP)-treated primates suggested that its use in human patients with IPD may augment the clinical benefits seen with levodopa. (Greenamyre, Id.) It is an embodiment of this invention that combining DOPA with remacemide in a metal complex will provide the kinetic synergy necessary to further augment the effects of both DOPA and remacemide as a treatment for PD, epilepsy, stroke and Huntington's disease.

Amantadine and its derivative memantine have been in clinical use of the treatment of PD for over 30 years. Likewise, dextromethorphan and dextrorphan are weak NMDA antagonists that have exhibited some clinical efficacy in alleviating levodopa-induced dyskinesias. (Marino, Id.) Rasagiline (Azilect) elicits a neuroprotective effect and is an irreversible, highly specific monoamine oxidase B (MAO-B) inhibitor approved in the United States in May 2006 as monotherapy for patients with PD or as an adjunctive therapy with levodopa. (Rao, Id.) The FDA approved the Zydis formulation of selegiline (Zelapar), another irreversible selective inhibitor of MAO-B, in June 2006 as adjunctive therapy for patients with a deteriorating response to levodopa. (E. V. Encarnacion & R. A. Hauser, Considerations in Neuroprotection in Parkinson's Disease, Medscape Neurology and Neurosurgery, 2007).

The NMDA receptor antagonists, dizocilpine, CPP [(R,S)-3-(2-carboxypiper-azin-4-yl)-propyl-1-phosphonic acid] and budipine, all potentiate the turning response induced by dopamine agonists in the 6-OHDA rat model. Budipine, a drug with a broad spectrum of action, is clinically useful in treating PD (Marino, Id.).

Development of a series of subunit-selective compounds related to ifenprodil has emerged from studies of NMDA receptors. Both ifenprodil and traxoprodil have been found to be effective antiparkinsonian agents in MPTP-lesioned primates. The AMPA antagonist NBQX (NNC079202) has shown promise as an adjunct to dopamine agonists. The competitive antagonists CPP an MDL 100453 [(R)-4-oxo-5-phosphononorvaline] have been indicated as potentiators of levodopa (Marino, Id.).

Activation of group I mGluRs by the group I mGluR-selective agonist DHPG [(R,S)-3,5-dihydroxyphenylglycine] induces direct effects on GP neurons including an inhibition of N- or P-type calcium conductances. The pharmacology of this direct depolarization has been determined using the mGluR1-selective antagonist LY367385 [(S)-(+)-a-amino-4-carboxy-2-methylbenzeneacetic acid], and the mGluR5-selective antagonist MPEP [2-methyl-6-(phenylethynyl)pyridine]. This depolarization is blocked by the mGluR5-selective antagonist MPEP, but not by the mGluR1-selective antagonist 7-(hydroxyimino)cyclopropa[b]chromen-1a-carboxylate ethyl ester (CPCCOEt), indicating that only one of the group 1 mGluRs (mGlueR5) localized at this synapse mediates the direct depolarization of these neurons (Marino, Id.).

Dopaminergic neurons have increasing reliance on $Ca^{2+}$ channels to maintain their autonomous activity. This has been posited to be contributing factor to the degeneration of dopaminergic neurons observed in Parkinson's disease patients. In fact, calcium channel blockers have been found to force dopaminergic neurons to maintain autonomous activity in a $Ca^{2+}$ independent manner. Moreover, the calcium channel blocker, isradipine, has been shown to provide neuroprotection against toxins known to illicit Parkinson's disease symptoms. (D. J. Surmeier, Calcium, Aging, and Neuronal Vulnerability in Parkinson's Disease, Lancet Neurol., 2007; 6(10), 933-8). Therefore, it is an embodiment of this invention that combining levodopa with a calcium channel blocker in a metal complex will provide the kinetic synergy to further augment the effects of both DOPA and the calcium channel blocker as a treatment for PD, epilepsy, stroke and Huntington's disease. It is preferred embodiment of this invention that the calcium channel blocker be selected from the class of drugs known as dihydropyridines. In a most preferred embodiment of this invention the dihydropyridine drug is isradipine.

Other specific examples of compounds that have shown to augment the actions of DOPA and thus are also candidates for FMDD as described as part of the embodiment of this invention include SIB 1893 [2-methyl-6-(2-phenylethenyl)pyridine], a selective mGluR5 antagonist structurally related to MPEP, the highly selective group II mGluR agonist LY354740 (eglumegad), which was shown to decrease haloperidol-induced muscle rigidity, the group II mGluR-selective agonist DCG-IV [(2S,2'R,3'R)-2-(2',3'-dicarboxycyclopropyl)glycine], which demonstrated a group II mGluR-specific reversal of reserpine-induced akinesia when injected intranigrally and the iron and copper chelating agents, carnosine and anserine. (Marino, Id.; J. H. Kang, Protection by Carnosine and Homocarnosine against L-Dopa-Fe(III)-Mediated DNA Clevage, Bull. Korean Chem. Soc., 2005, 26 (8), 1251-1254).

Inosine is a precursor of urate, which is deficient in PD patients and both urate and inosine have been studied as possible treatments to slow the progression of PD. Désirée Lie, Urate Slows Progression of Parkinson's Disease, Medscape Medical News, 2008. Creatine is also been found to slow the progression of PD. Thus, inosine, creatine and urate are also candidates for FMDD as described as part of the embodiment of this invention.

Alzheimer's Disease

A recent study found that memory loss due to degenerative brain diseases, including Alzheimer's, may be reversible with the help of mental stimulation and use of drugs. The study (Nature), which was carried out by researchers at the Massachusetts Institute of Technology (MIT), found that genetically engineered mice with a triggered protein linked to degenerative brain disease that resulted in an Alzheimer-like condition were able to regain memories of tasks they had previously been taught with the help of two methods: brain stimulation and drugs. The damage was inflicted in the mice through the specific neural networks in the brain and the scientists achieved the same regenerative results through a drug treatment. The researchers also tested histone deacetylase (HDAC) inhibitors on the mice, which seemed to improve memory and learning, similar to improvements made by environmental stimulation. (A. Fischer et al., Recovery of Learning and Memory is Associated with Chromatin Remodelling, Nature, 2007, 447 (7141), 178-82).

It is yet to be determined if the same techniques would work in humans but scientists are optimistic at the possibility of recovering long-term memories in patients whose brains suffered certain neurological disorders. Thus it seems that memories are not erased from the brain, but rather are made inaccessible by the disease.

While early high-affinity, uncompetitive NMDAR antagonists certainly caused deterioration in Alzheimer's patients, lower-affinity, un- or noncompetitive antagonists like memantine (and remacemide) have been shown not to interfere with normal synaptic transmission and to actually improve cognition in Alzheimer's patients while offering neuroprotection against disease progression.

Proteins with expanded polyglutamine repeats are implicated in the transcriptional dysfunction that is believed to be an important pathogenic mechanism of many neurodegenerative diseases including Alzheimer's. In particular the loss of function of the transcriptional co-activator CREB-binding protein (CBP) is of particular note in the etiology of these diseases. It has been proposed that over-expression or loss of function of CBP will result in synaptic transmission defects. This seems to demonstrate that there is a critical balance required for CBP for proper synaptic transmission and that countering CBP binding (i.e. reduced acetylation of histones) with HDAC inhibition could provide the right balance of CBP activity. Recently it has been reported that the polyglutamine-containing domain of specific protein, Huntingtin, causes a reduction in the level of acetylation of histones and that this effect can be reversed by administration of HDAC inhibitors. (L. M. Thompson et al., Histone Deacetylase Inhibitors for Reducing Polyglutamine Toxicity In vivo, Provisional Patent Applications, 2001).

Glutamic acid and aspartic acids are the physiological mediators of most excitatory synaptic transmission. The synaptic balance that is critical for proper regulation of polyglutamine is thus regulated by these neurotransmitters. The NMDA receptors are a critical component of metabotropic glutamate receptors, responsible for increases in calcium and sodium fluxes. Intracellular calcium overload is one signal for neuronal death. In addition to polyglutamine, other mediators of synaptic transmission that operate on the NMDA receptor, such as nitric oxide, arachadonic acid, super oxide are also mediators of neuronal death. (R. J. Thomas, Excitatory Amino Acids in Health and Disease, J. Am. Geriatr. Soc., 1995, 43 (11), 1279-89). The entire synaptic balance is influenced by all of these neurotransmitters and receptors, particularly the NMDA receptors, which interact with the expression of gene products, of which CBP and, consequently HDAC, are intimately involved. Thus it stands to reason that a very effective application of this FMDD concept would be a combination of an NMDA receptor antagonist like remacemide and an HDAC inhibitor like SAHA. Moreover, it has been proposed that anti-CBP gene products that lead to apoptosis are potentiated by highly active NMDA receptors. Thus it appears that HDAC mediated gene products and NMDA receptors are intrinsically linked to the etiology of Alzheimer's disease and related neurological disorders.

It is an embodiment of this invention, therefore, that an HDACi-metallo-NMDAR inhibitor complex provides potentiated treatment for Alzheimer's disease and related disease states beyond what the individual components could. It is a further embodiment of the invention that SAHA-metal-remacemide represents a new combination of drugs combined to potentiate their respective efficacies in treating Alzheimer's and related disease states. In a most preferred embodiment of the invention the FMDD drug complex is SAHA-Mg-remacemide.

L-methylfolate is being marketed for treatment of peripheral neuropathy, depression and Alzheimer's dementia by Pamlab. It is an NMDAR antagonist and easily crosses the blood brain barrier. Thus it is an embodiment of this invention that SAHA-metal-methylfolate represents a new combination of drugs combined to potentiate their respective efficacies in treating Alzheimer's and related disease states. In a most preferred embodiment of the invention the FMDD drug complex includes SAHA-Mg-methylfolate.

Carnosine (beta-alanyl-L-histidine) is a naturally-occurring dipeptide which, along with zinc, typically enriches the olfactory lobe. Carnosine has been shown to suppress amyloid-beta peptide toxicity, inhibit production of oxygen free-radicals, scavenge hydroxyl radicals and reactive aldehydes, and suppress protein glycation, which may all contribute to the pathophysiology of Alzheimer's Disease and other neurodegenerative diseases. Further, zinc accumulation is a prominent feature of advanced Alzheimer disease and has been linked to brain amyloid β-peptide aggregation and dementia severity.

It is thus an additional embodiment of this invention that carnosine-metal-HDACi, carnosine-metal-NMDAR inhibitor and carnosine-metal-methylfolate FMDD drug complexes could synergistically potentiate the respective therapeutic utilities of these agents. Also, given the zinc-chelating properties of carnosine and that magnesium itself effectively acts as an inorganic calcium-channel blocker and could amplify NMDA receptor blockade, the most preferred embodiment of these additional inventions are carnosine-Mg-remacemide and carnosine-Mg-methylfolate.

Epilepsy

A report of a combined treatment of the potent non-competitive NMDA-R antagonist dizocilpine with valproate, which provided a 50% protection against MES induced seizures, also produced a ~3-fold reduction in the $ED_{50}$ of valproate. In addition, some of the valproate-induced side effects could not be observed when the combination with valproate was used. (B. K. Kohl & G. Dannhardt, The NMDA Receptor Complex: A Promising Target for Novel Antiepileptic Strategies, Curr. Med. Chem., 2001, 8 (11), 1275-89).

Synergism between the polyamine site antagonist, eliprodil, and the $glycine_B$ receptor antagonist, L-701,324, was observed in the amygdala kindling model in rats (Kohl & Dannhardt, Id.). Thus it is an embodiment of this invention that polyamine site antagonist and $glycine_B$ receptor antagonists potentiate each other in accordance to the premise of this invention through metal coordination. In a preferred embodiment of the invention the FMDD complex includes eliprodil-metal-(L-701,324).

Carnosine can protect against PTZ-induced seizures and acts mainly through the carnosine-histidine-histamine metabolic pathway. (Y. Y. Zhu et al., Carnosine Inhibits Pentylenetetrazol-induced Seizures by Histaminergic Mechanisms in Histidine Decarboxylase Knock-out mice, Neurosci. Lett., 2007, 416 (3), 211-6). Thus, carnosine, once more, is implicated as a key FMDD ligand in potentiating the effects of drugs acting on the central nervous system. Nipecotic acid has also been tested on PTZ-induced convulsions in rats, and thus, is also a potential FMDD ligand in the treatment of epilepsy.

Nearly 30% of epilepsy sufferers have seizures that are refractory to currently available drugs. In response to these refractory conditions, new anti-epileptic drugs, such as remacemide, are being developed. In one study, remacemide inhibited glutamatergic transmission by blocking NMDA receptors while lamotrigine exerted preferential pre-synaptic action. Thus, coadministration of low doses of both drugs provided additive neuroprotective properties. Moreover, in addition to lamotrigine, remacemide has been studied as a combination therapy with phenyloin, felbamate, gabapentin, oxcarbazepine, vigabatrin, zonisamide and valproic acid. FMDD-designed combinations of these agents are contemplated by this invention. (P. Calabresi et al., Lamotrigine and Remacemide Protect Striatal Neurons Against In Vitro Ischemia: An Electrophysiological Study, Exp. Neurol., 2003, 182 (2), 461-9; J. P. Leach et al., Mutual Interaction Between Remacemide Hydrochloride and Phenyloin, Epilepsy Res., 1997, 26 (2), 381-8; J. P. Leach et al., Lack of Pharmacokinetic Interaction Between Remacemide Hydrochloride and Sodium Valproate in Epileptic Patients, Seizure, 1997, 6 (3), 179-84).

Multiple Sclerosis

Multiple sclerosis (MS) is an inflammatory autoimmune disease that progresses through demyelination and axonal loss in the brain and spinal cord. The etiology and progression of MS involves various pathomechanisms, which include immune-related inflammatory cascade, oxidative toxicity and excitotoxicity. Moreover, the disease has multiple levels of damage, wherein destruction of myelin-producing oligodendrocytes follows a different pathology than the mechanisms that mediate axonal and neuronal damage.

The pathogenesis of the disease is believed to be initiated by the antigen activation of autoreactive T lymphocytes, which after penetration through the BBB cause secretion of pro-inflammatory cytokines. The activity of these cytokines results in recruitment of circulating lymphocytes and monocytes and their transformation into macrophages. This sets up a cascade of events including myelin phagocytosis, inflammatory signals and expression of apoptotic gene products, all of which lead to the damaging effects characterized by MS. Thus the beneficial effect of an MS drug can intervene anywhere in this cascade of events including the application of anti-inflammatory mediators. (B. Weinstock-Guttman & R. Bakshi, Combination Therapy for Multiple Sclerosis: The Treatment Strategy of the Future?, CNS Drugs, 2004, 18 (12), 777-92). For example, an agent that augments immunomodulation of myelin-reactive T cells toward Th2 differentiation could be beneficial.

Therapeutic agents for the treatment of MS are typically focused on the immune-mediated inflammatory cascade and oxidative toxicity. (R. E. Gonsette, Combination Therapy for Multiple Sclerosis, Int. M. S. J., 2004, 11 (1), 10-21). Acute symptomatic attacks and relapses followed by periods of remission, also known as relapsing-remitting multiple sclerosis (RRMS), are typically treated with high-dose intravenous steroids such as methylprednisolone which acts to dampen the inflammatory cytokine cascade, decreases the extravasation of activated immune cells into the central nervous system, suppresses the activation of destructive T-cells, and reduces the cytotoxic effects of nitric oxide and tumor necrosis factor. Disease modifying agents include various interferons, glatiramer acetate, mitoxantrone and natalizumab, a humanized monoclonal antibody integrin antagonist. (Weinstock-Guttman, Id.) Fumaric acid esters have also been shown to inhibit activated macrophage migration, adhesion, and extravasation in MS patients with active disease and may have a future role in chronic oral suppressive therapy.

The strategies currently used for multidrug therapies in MS include fixed dose combination therapy for targeting distinct pathomechanisms or sequential addition of drugs to maintain or potentiate the efficacy of the first drug administered. These include concurrent use of methylprednisolone with immunosuppressive agents such as mitoxantrone and azathioprine, beta interferon (IFNβ) with glatiramer acetate, and IFNβ/natalizumab combination therapy (Gonsette, Id.). Oftentimes, however, these combinatorial strategies do not manifest the effectiveness that is desired or manifest serious adverse side effects that may be due to the fact the administration of the MS drugs are not kinetically synergistic.

For example, by also altering the expression of adhesion molecules and preventing leukocyte migration across the blood-brain-barrier, IFNβ may potentiate natalizumab's antagonism of integrin within the CNS and reduce the inflammatory cascade leading to demyelination in refractory cases. This nonspecific and uncontrolled potentiation, however, may lead to the development of progressive multifocal leukoencephalopathy (PML) in these patients, an often fatal opportunistic viral disease. (H. H. Salama et al., Effects of Combination Therapy of Beta-interferon 1a and Prednisone on Serum Immunologic Markers in Patients with Multiple Sclerosis, Mult. Scler., 2003, 9 (1), 28-31).

The premise of this invention is that by combining two or more MS drugs as a single molecular entity, effectively delivering therapies in a more controlled and discrete synergistic fashion, strategies addressing multiple pathomechanisms can be more effectively designed and implemented without problematic over-potentiation of targeted pathways. It is an embodiment of this invention, therefore, that combining two or more drugs with a metal to form a single molecular entity metal coordination complex has the proper FMDD properties to treat separate pathomechanisms associated with MS with the optimum kinetic synergy to potentiate the effects of the MS drugs that are a part of the metal coordination complex.

It is additionally believed that IFNβ works on MS via its anti-proliferative effects, suppression of pro-inflammatory cytokines, and the effects on matrix metalloproteinases. Glatiramer acetate is believed to inhibit specific effector T-lymphocytes and induce suppressor T-lymphocytes, thus combining glatiramer acetate with IFNβ fits with the multiple mechanistic approaches and has demonstrated an additive effect in vitro. (M. J. Tullman & F. D. Lublin, Combination Therapy in Multiple Sclerosis, Curr. Neurol. Neurosci. Rep., 2005, 5 (3), 245-8).

Statins have anti-inflammatory and neuroprotective properties; lovastatin and atorvastatin protect animals against both acute and remitting-relapsing (RR) experimental autoimmune encephalomyelitis (EAE) disease via attenuation of the neuro-inflammatory CNS response and the promotion of the Th2 differentiation of the naive myelin-specific T-cells. Treatment of CNS glial cells with the AMP activated protein kinase (AMPK) activator, 5-aminoimidazole-4-caboxamide-1-B-D-ribofuranoside (AICAR), protected against lipopolysaccharide-induced pro-inflammatory response. Combination therapy with suboptimal doses of lovastatin and AICAR additively reversed or prevented EAE in animals by reducing disease severity, CNS inflammation and neurodegeneration, compared with animals treated with either drug alone at the same dose. (A. S. Paintlia et al., Immunomodulatory Effect of Combination Therapy with Lovastatin and 5-aminoimidazole-4-carboxamide-1-beta-D-ribofuranoside Alleviates Neurodegeneration in Experimental Autoimmune Encephalomyelitis, Am. J. Pathol., 2006, 169 (3), 1012-25).

Combination therapy with suboptimal doses of lovastatin and AICAR complement each other by reversing pro-inflammatory responses in the CNS of EAE. Moreover the combination of the two agents reverses pathological changes and cellular infiltration, promotes expression of anti-inflammatory immune response, promotes induction of myelin-reactive Th2 cells and alleviates neurodegeneration in the CNS of EAE animal models (Paintlia, Id.). Moreover, axonal and neuronal degeneration in inflammatory autoimmune CNS disorders can be prevented by a combination of a neuroprotective agent, such as erythropoietin, and a steroid, such as methylprednisolone, during the acute stage of the disease. (R. Diem et al., Combined Therapy with Methylprednisolone and Erythropoietin in a Model of Multiple Sclerosis, Brain, 2005, 128 (Pt 2), 375-85).

The premise of combining drugs in an MS application or RRMS application as described in this invention can be applied to other drugs which are used to treat MS either alone or in combination. This is especially true considering that combination MS drugs are touted to work best when different mechanisms of treating the disease are addressed. So, for example, fingolimod, which has shown great promise for the treatment of relapsing multiple sclerosis, imparts its immunosuppressive effects by preventing the egress of lymphocytes from lymph nodes. (L. Kappos et al., Oral Fingolimod (FTY720) for Relapsing Multiple Sclerosis, N. Engl. J. Med., 2006, 355 (11), 1124-40). Mitoxantrone also has immunosuppressive properties but its mechanism of immunosuppression differs from that of fingolimod.

Methotrexate is an immuno-modulatory and an anti-inflammatory agent. Azathioprene immuno-modulates both T and B cells and is being considered as an adjunct therapy in patients with RRMS who do not respond to glatiramer acetate or IFNβ. Intravenous immunoglobulin has been used to treat autoimmune neurological diseases but not MS. Perhaps the application of FMDD to a combination of immunoglobulin with another MS drug can be used to treat MS or RRMS. Perhaps a combination of any two or more drugs, most of which have different mechanisms of action anyway, can be combined to treat MS or RRMS. It is an embodiment of this invention that the combination drugs to treat MS or RRMS will be potentiated when the combination is metal coordinated to produce an FMDD complex.

Other drugs that have been studied as combination therapies to treat MS include fumaric acid esters, daclizumab, matrix metalloproteinases, erythropoietin, cyclophosphoramide, valacyclovir, mycophenolate, tacrolimus, pentoxifylline, retinoic acid, fluoxetine, acetaminophen, ibuprofen, prednisone, inosine, selegeline, metacycline, pencillamine, tiazfurin, ribavirin and mizoribine. FMDD-designed complexes of these agents are contemplated by this invention.

Schizophrenia

Rorick-Kehn, et. al. describe a mGlu 2/3 agonist, which is a conformationally locked fused ring glutamic acid derivative. (L. M. Rorick-Kehn et al., Pharmacological and Pharmacokinetic Properties of a Structurally Novel, Potent, and Selective Metabotropic Glutamate 2/3 Receptor Agonist: In Vitro Characterization of Agonist (−)-(1R,4S,5S,6S)-4-amino-2-sulfonylbicyclo[3.1.0]-hexane-4,6-dicarboxylic Acid (LY404039), J. Pharmacol. Exp. Ther., 2007, 321 (1), 308-17). The compound LY404039, may be beneficial for treatment of schizophrenia and anxiety. It works by selectively causing subtle alterations in neuron transmission resulting in the suppression of pathological glutamate release without affecting normal synaptic transmission. Thus it does not produce unwanted side effects typically found with benzodiazepines and neuroleptics, such as sedation, abuse liability, dependence and motor side effects. Since this drug modulates excessive glutamate release, which is the cause for the side effects of other drugs, LY 404039 could potentiate the effects of other anti-psychotics by both ameliorating the glutamate release and lowering the dose through a neurotropic effect. Thus an FMDD-designed complex of an mGlu 2/3 agonist with other anti-psychotics is anticipated by this invention.

Learning Disabilities and Autism Spectrum Disorders

Learning disabilities and Autism Spectrum Disorders are a heterogeneous group of diseases variably characterized by an impaired ability to learn, speak, listen, read, write, spell, reason, organize information, and achieve appropriate social awareness. While recognizing the numerous disparate etiologies and varied clinical presentations within pediatric and adolescent populations, the final common pathway of the diverse cognitive dysfunction characterizing these disorders may be viewed as physiological dysfunction of the ion channels, synapses and neural networks which comprise the core of the maturing central nervous system. In particular, growing evidence suggests that recessive mutations in highly conserved ion channel protein domains result in, in effect, ion channelopathies with altered synaptic transmission and resultant neuropsychiatric dysfunction.

Specifically, mutations of both voltage-gated and ligand-gated ion channels that regulate neuronal excitability and calcium-regulated signaling proteins have been associated with the development of autism and other related disorders. Additionally, it has been shown that selective antagonism of NMDA receptors in mice impairs acquisition of spatial learning behavior, while synchronous stimulation of both NMDA and AMPA receptors appear to be critical for normal excitatory synaptic transmission and plasticity throughout the developing brain and spinal cord. This suggests that a subtle, but synergistic, interplay exists between excitatory neuroreceptors, as well as an intrinsic susceptibility to over-stimulation by asynchronous release of excitatory amino acids, mainly glutamate and aspartate.

For example, Michael Chez and colleagues have recently demonstrated that use of memantine, a moderate-affinity antagonist of NMDA receptors, in patients diagnosed with autism showed significant improvement in language function, social behavior and self-stimulatory behaviors. These benefits were hypothesized to be attributable to blockade of excessive glutamate which leads to neuroglial inflammation and aberrant neuronal migration, differentiation and development in the maturing brain. (M. G. Chez et al., Memantine as Adjunctive Therapy in Children Diagnosed With Autistic Spectrum Disorders: An Observation of Initial Clinical Response and Maintenance Tolerability, J. Child Neurol., 2007, 22 (5), 574-9). Thus, kinetic modulation of NMDA and AMPA receptors in a physiologically synergistic fashion could improve language development and social behavior in individuals with autism and other related disorders.

Chez has further found that use of carnosine in children with autism and other related disorders demonstrate improved neurobehavioral function due to its activating and neuroprotective affects on the frontal lobe. Via direct chelation of zinc and copper, carnosine may reduce zinc's inhibitory affects on NMDA and GABA receptor-mediated synaptic transmission as well as the damaging influx of zinc and copper into the hippocampus and frontal lobes. This modulation of metal cations inhibits the epileptiform activity seen in one-third of autistic patients and may improve impairments in expression and behavior associated with autistic-related frontal lobe dysfunction. Trials combining the concurrent use of memantine and carnosine in afflicted patients are currently ongoing and preliminarily show objective measurable improvements in speech reception, socialization and behavior again suggestive of synergistic potentiation of these individual therapeutic agents.

It is thus an embodiment of this invention that a FMDD complex for the treatment of autism and other related disorders be comprised of an NMDA receptor antagonist, magnesium as a potentiator of NMDA antagonism, and carnosine. Preferred embodiments of this invention would therefore be remacemide-magnesium-carnosine, as well as remacemide-magnesium-curcumin due to curcumin's known anti-oxidant and anti-inflammatory properties within the central nervous system. In the same respect, another preferred embodiment of this invention would be remacemide-magnesium-glutathione due to glutathione's similar ability to suppress oxidative injury.

Other FMDD complexes envisioned by this invention include the combination of AMPA receptor agonists and antagonists along with a chelating metal and NMDA receptor antagonists, carnosine, curcumin, glutathione and methylfolate. Also, the FMDD complex of metabotropic glutamate (mGlu5) receptor antagonists along with a chelating metal and NMDA receptor antagonists, carnosine, curcumin, glutathione and methylolate are also contemplated. D-cycloserine, a partial agonist at the glycine site of NMDA receptors with differing affinities for NMDA receptor subtypes, has been positively associated with improvement in social withdrawal symptoms in autistic children. (D. J. Posey et al., A Pilot Study of D-cycloserine in Subjects With Autistic Disorder, Am. J. Psychiatry, 2004, 161 (11), 2115-7). It is thus an additional embodiment of this invention that D-cycloserine is combined with carnosine, curcumin, glutathione or methylfolate along with a chelating metal in a FMDD complex.

Kinetic modulation of mGlu5-specific receptors, in addition to other metabotropic glutamate receptors, is of special interest due to the observations that mGlu5-specific receptor antagonism mimics clinical NMDA receptor dysfunction (such as schizophrenia and addictive disorders), possesses unique anxiolytic and anticonvulsant properties, and has been shown to successfully treat patients with Fragile X mental retardation. Additionally, blockade of these G-protein coupled receptors appear to attenuate NMDA receptor-mediated postsynaptic excitability in the hippocampus, again suggestive of a kinetic interplay between these receptors that would be amenable to synergistic modulation by FMDD-designed metallo-pharmaceutical complexes.

Pentylenetetrazole (PTZ) has recently been shown to improve learning and memory in patients with Down's Syndrome. Historically, PTZ has been used as a circulatory and respiratory stimulant, and used experimentally as a chemical kindling agent to induce and study seizure phenomenon in animals due to its antagonistic GABA receptor properties. In Down's Syndrome patients, it is hypothesized that PTZ's antagonism of GABA's exaggerated inhibitory effects may improve neuronal and synaptic transmission and thus promote the acquisition, processing and retention of novel information. (F. Fernandez et al., Pharmacotherapy for Cognitive Impairment In a Mouse Model of Down Syndrome, Nat. Neurosci., 2007, 10 (4), 411-3).

It's been also observed that carnosine is protective against PTZ-kindled seizures in rats via the carnosine-histidine-histamine metabolic pathway. It is therefore an additional embodiment of this invention that a FMDD complexation of PTZ-magnesium-carnosine may promote the acquisition, processing and retention of information in Down's patients and other patients with learning disabilities, while suppressing the deleterious chemical kindling and seizure activity that may be precipitated by PTZ usage. Additionally, synergistic potentiation of these pathways by combining PTZ with a NMDA receptor antagonist in a FMDD complex configuration due to its antiepileptic activity and its attenuation of glutamate-induced excitotoxicity is also contemplated by this invention.

Use in the Treatment of Cancer

Combination therapies are increasingly being used to treat various forms of cancer. For example, the recent advent of antiangiogenesis reagents provided a new and effective treatment option for various cancer types. It has been discovered, however, that tumor cells develop a resistant phenotype when subjected to the hypoxic conditions that antiangiogenesis reagents create. The resultant refractory condition can be treated with combinations of antiangiogenesis and conventional cytotoxic agents such as cisplatin, carboplatin, gemcitabine, fluorouracil or taxanes. Concomitant treatment may reduce the dosing requirement for the antiangiogenesis reagent, which may reduce the potential for cell mutation and allow the needed vascularization for delivery of the cytotoxic reagent. Thus, fluorouracil and leukovorin have been used as combination therapy to treat colorectal cancer.

Although unrelated mechanistically, other specific examples of combination cancer therapies include the CHOP and MOPP protocols for non-Hodgkins and Hodgkins lymphomas, BEP for testicular carcinoma and antiandrogens combined with GnRH agonist such as goserelin or leuprolide.

Prostate Cancer

Whereas each of these anticancer cocktails are more potent as combinations, the synergy between them is limited mechanistically. There are anticancer agents that when combined in a single therapeutic regimen are very effective but their efficacy could be further improved if the synergy between the reagents could be kinetically controlled, that is the different agents in the cocktail were to reach their target receptor or cofactor with well coordinated timing. Antiandrogen therapy combined with histone deacetylase inhibitors is an example where the two reagents when combined in a kinetically controlled synergistic manner would exhibit enhanced effectiveness in treating prostate cancer.

Antiandrogen therapies remain a very viable approach to treating prostate cancer, notwithstanding some of the adverse effects seen with their use. Many patients undergoing this treatment regimen may determine that the treatment's benefits outweigh the adverse effects and justify its discomfort and risk.

One of the major problems that exist with many anticancer therapies, particularly antiandrogen therapy, is that patients often become resistant to the drug. The risk of becoming refractory may not halt treatment, but refractory prostate cancer is a very difficult disease to manage. Secondary hormone therapy, chemotherapy and bisphosphonate therapy have been recommended as a second line of treatment for a select population of patients who no longer respond sufficiently to antiandrogen therapy. (M. Diaz & S. G. Patterson, Management of Androgen-independent Prostate Cancer, Cancer Control, 2004, 11 (6), 364-73). These options may not be the best ones available and a method of prolonging the efficacy of antiandrogens, particularly bicalutamide, may prove to be the best-in-class approach to refractory prostate cancer.

The postulated mechanisms to explain why patients undergoing antiandrogen therapy become refractory include 1) androgen receptor genes mutate causing the antiandrogen to behave as an agonist; 2) oncogene mediated MAP kinase signaling increases causing ligand-independent activation of the androgen receptor and 3) growth and survival functions of the androgen receptor are bypassed rendering the androgen receptor no longer relevant to disease progression.

Ligand-independent activation of the androgen receptor is believed to be due to its over expression. Androgen receptor must bind its ligand to confer hormone-refractory growth, and a modest increase in receptor concentration permits the receptor to function despite lower levels of androgens, such as in castrated patients or patients taking GnRH. This is likely due to alterations in the balance between coactivators and corepressors that can affect androgen receptor activation. (C. D. Chen et al., Molecular Determinants of Resistance to Antiandrogen Therapy, Nat. Med., 2004, 10 (1), 33-9).

This disruption of the balance of gene expression regulators also plays a role in the refractory mechanism in those cases when the antagonist behaves like an agonist. The mechanism of hormone-refraction being due to antagonist-to-agonist switch was supported by hormone-refractory tumors having more androgen receptor protein than their parental hormone-sensitive counterparts. Furthermore, it was found that this antagonist-to-agonist conversion was not unique to bicalutamide or particular hormone-refractory cell lines (Chen, Id.). Thus, the mechanism of hormone refractory antiandrogen therapy is somewhat ubiquitous amongst cancer cell lines and is not relegated to a single receptor class.

Long term and continued exposure of androgen receptor containing cells to bicalutamide treatment causes an increase in the amount of androgen receptors that are expressed. An increase in the number of androgen receptors will increase the variation in their expression and shift the relative abundance of coactivators and corepressors assembled on the promoters of androgen receptor genes. This leads to the decreased ability to recruit the necessary coactivators necessary for transcription of gene products that shut down production of cancer causing genes.

Whereas RNA polymerase or histone acetylation was not recruited to promoters in response to bicalutamide in cells with normal amount of androgen receptors, polymerase II was present in cells with excess androgen receptor treated with bicalutamide (Chen, Id.). This implies that histone acetylation may also play a role in the shifting of the relative abundance of coactivator and corepressors. Since chronic exposure of androgen receptors to bicalutamide initiates a cascade of events leading to a disruption of the mode of action of those receptors, keeping bicalutamide dose low or potentiating its effect with another anticancer drug may prevent increased androgen receptor expression.

Histones are protein structures that make up chromatin, which wraps around the DNA molecule. They are that part of the nucleosome that is directly involved in the regulation of gene product expression. When the lysine residues on histones are charged, the chromatin tightens up on the DNA strand, thereby preventing expression of the gene products on the DNA. Neutralization of the histone charge, primarily by acetylation of the lysine residues, loosens the chromatin from the DNA, allowing for the DNA to transfer its message to RNA and ultimately allowing gene expression.

The facilitation of gene expression by the acetylation of histone is catalyzed by histone acetyltransferase (HAT). Conversely, the shut down of gene expression through a reverse acetylation process or deacetylation, as it is referred, is catalyzed by histone deacetylase (HDAC). HDACs restore the positive charge on lysine residues by removing acetyl groups and thus are involved primarily in the repression of gene transcription by compacting chromatin structure. (M. R. Acharya et al., Rational Development of Histone Deacetylase Inhibitors as Anticancer Agents: A Review, Mol. Pharmacol., 2005, 68 (4), 917-32).

The discovery of the acetylation of histone to regulate gene expression has opened up many areas of research including the application of this biochemical machinery to gene regulated antineoplastic agents. The majority of work in this area has focused on inhibiting HDAC.

The general effect of HDAC inhibitors (HDACi) often seen in cell lines is cytotoxicity, differentiation, inhibition of proliferation and induction of apoptosis. (A. J. de Ruijter et al., Histone Deacetylases (HDACs): Characterization of the Classical HDAC Family, Biochem. J., 2003, 370 (Pt 3), 737-49). Treatment of tumor cells with HDAC inhibitors triggers both the intrinsic pathway and sensitizes tumor cells to the death ligands that initiate the extrinsic pathway of apoptosis. (K. Bhalla & A. List, Histone Deacetylase Inhibitors in Myelodysplastic Syndrome, Best Pract. Res. Clin. Haematol., 2004, 17 (4), 595-611). Cancer can result from inappropriate silencing of critical genes leading to inactivation of tumor suppressor gene (TSG). The reactivation of TSG by allowing the expression of the critical genes through inhibition of HDAC has enormous potential for preventing and treating cancer (Acharya, Id.).

For example, when six cancer cell lines were pretreated with HDAC inhibitors followed by treatment with a variety of cancer drugs that target chromatin DNA, there was a more than ten-fold sensitization of cells. The data suggested that loosening up the chromatin structure by histone acetylation can increase efficiency of several anticancer agents. A very widely studied HDACi, suberoylanilide hydroxamic acid (SAHA), significantly potentiated the DNA damage by topoisomerase II inhibitors; however the synergy was dependant on the sequence of drug administration and expression of target (Acharya, Id.).

As alluded to earlier, androgen receptor actions seems to be mediated exclusively through genotropic mechanisms, thus one can also envision drugs that present androgen receptor nuclear translocation or impair assembly of androgen receptor transcription complexes on target genes (Chen, Id.). The effect of HDACi on gene expression is believed not to be a general one, but rather involves alteration of the transcription of a specific subset of genes (de Ruijter, p. 746).

HDAC responsive genes belong to the cell cycle, apoptosis, and transcription factor classes. De Ruijter identified a myriad of other responsive genes including genes for matrix metalloproteinase-2, interleukin-6 receptor, interleukin-2, -8 and -10, intercellular cell-adhesion molecule-1, carboxypeptidase A3, human telomerase reverse transcriptase and vascular endothelial growth factor. De Ruitjer did not expressly identify androgen-sensitive genes but since it is known that HDACi prevents androgen antagonist resistance, the two anticancer agents are intrinsically linked (de Ruijter, Id.). It is possible that the coactivators involved in transcription due to antiandrogen receptor ligation are promoters of HDAC. This premise is supported by the fact that when the HDAC inhibitor, 7-phenyl-2,4,6-hepta-trienoyl hydroxamic acid, was combined with bicalutamide, an additive effect on growth inhibition and apoptosis in androgen resistant prostate cancer cells was found. It was also shown that this HDACi worked synergistically with bicalutamide on growth inhibition of cancer cells.

It appears that bicalutamide's ability to block the androgen receptor from suppression of anticancer gene product transcription (i.e. recruiting required coactivators for transcription) can be potentiated by the synergistic introduction of an HDACi, another agent that promotes transcription. In other words, the genetic events that are connected with blocking the androgen receptor are intrinsically linked to the mechanisms associated with activation of gene transcription. Furthermore, inhibition of HDAC may suppress the events responsible for the shifting in the coactivator and corepressor recruitment linked to antiandrogen resistance.

Potentiating the effects of an antiandrogen through promotion of transcription by HDAC inhibition of intrinsically linked gene products is best accomplished if the effects of the two reagents were kinetically linked. Thus, the key element in the optimum synergistic combination of antiandrogens and HDAC inhibitors is that that the two anticancer agents are introduced to the cancer cells simultaneously. This is best accomplished if the antiandrogen and the HDACi are presented to the cell as a single molecular entity.

Delivering an antiandrogen drug and an HDACi to the cell as a single molecular entity can be accomplished by covalently attaching a linker to each of the anticancer reagents. It would be unlikely, however, for the HDACi to migrate to the nucleus when it is attached to the antiandrogen that is bound to the receptor. Therefore a cancer therapy that would allow the combination therapies to work in concert yet not affect the efficacy of the individual components would have a distinct advantage over a drug where the two reagents were combined in a more permanent covalent bond.

Bicalutamide and hydroxamic acid can form stable metal coordinated complexes. A metal complexed with a hydroxamic acid derived HDACi and bicalutamide, or its chemical and pharmacologic equivalent, would have sufficient stability to reach the cancer cell as an intact hetero-ligated complex but would breakdown and release the metal and HDACi upon interaction with the androgen receptor. The HDACi would then transfect the cell membrane and migrate to the nucleus as usual and promote transcription of gene products that potentiate the effect of the androgen antagonist. Thus it is an embodiment of this invention that an antiandrogen drug and an HDACi drug complexed with a metal are delivered to the androgen receptor, thereby releasing the HDACi to the nucleus in a kinetically controlled manner to impart optimum synergy between the reagents and thereby prevent the onset of a refractory condition.

Both bicalutamide and hydroxamic acid have been shown to chelate metals. Since some hydroxamic acids are siderophores the ideal metal may be iron. Therefore, it is an embodiment of the invention that the biologically synergistic anticancer reagent consist of an antiandrogen, such as bicalutamide, and a hydroxamic acid class of HDAC inhibitor, such as SAHA, and a metal that will form a stable complex with both anticancer ligands. It is a preferred embodiment of the invention that the metal be iron.

The application of metal coordination to optimize synergistic effects between two or more anticancer reagents is not limited to antiandrogens. In one study, it was proposed that HDACi might activate components of the death receptor pathways in various solid tumors. Furthermore, it was shown that in several cases apoptosis of tumor cell lines was induced through synergistic action of HDACi with exogenously added tumor necrosis factor-related apoptosis inducing ligand (TRAIL). (S. Minucci & P. G. Pelicci, Histone Deacetylase Inhibitors and the Promise of Epigenetic (and more) Treatments for Cancer, Nat. Rev. Cancer, 2006, 6 (1), 38-51).

Another report proposed that since HDAC inhibitors induce cell cycle arrest through the induction of certain tumor suppression genes (e.g., p21$^{WAF1/CIP1}$), that colon cancer and lung cancer cells would be sensitized to TRAIL-induced lethality. It was discovered, however, that when cells were simultaneously exposed to HDAC inhibitors with TRAIL, as opposed to sequential exposure, a large increase in apoptosis was obtained. This study also suggested the importance of incorporating a kinetic component to synergistic application of anticancer agents. The researchers believed that co-administration of TRAIL with HDAC inhibitors indicated simultaneous activation of the extrinsic and intrinsic pathways leading to a dramatic increase in mitochondrial injury and activation of caspase cascades. This was supported by earlier studies that showed that TRAIL enhances the antitumor activity of multiple convention cytotoxic drugs, which primarily act through the intrinsic/mitochondrial pathway, including etoposide, cytosine arabinoside, cisplatin, doxorubicin and paclitaxel. (R. R. Rosato et al., Simultaneous Activation of the Intrinsic and Extrinsic Pathways by Histone Deacetylase (HDAC) Inhibitors and Tumor Necrosis Factor-related Apoptosis-inducing Ligand (TRAIL) Synergistically Induces Mitochondrial Damage and Apoptosis in Human Leukemia Cells, Mol. Cancer. Ther., 2003, 2 (12), 1273-84).

Moreover, the antisense molecule, custirsen has shown potential in combination with either docetaxel or mitoxantrone to treat hormone refractory prostate cancer. Thus the combination of a TRAIL with an HDAC inhibitor and a metal that will form a stable complex with both anticancer ligands is an embodiment of the invention.

Leukemia

It is a further embodiment of this invention that treatment for acute promyelotic leukemia (APL) can be realized through FMDD complex application of retinoic acid (RA) and an HDACi. Promyelotic leukemia zinc finger (PLZF) does not respond to RA treatment because the RA will not turn on the conformational switch that leads to the release of HDAC-containing complexes, which ultimately lead to powerful bursts of differentiation; this is counter to hyperproliferation associated with cancer malignancies. However, the combination of RA with HDACi is extremely effective in reactivating RA target genes and triggers a cellular response in vitro and in vivo in PLZF-RAR-positive APL patients. In fact, the HDACi, phenylbutryate, was used in combination with RA to treat a 13 year old girl with relapsed APL.

In a further embodiment of this invention, HDAC inhibitors can be synergistically combined with antimetabolites through metal coordination to potentiate the antileukemic effect of each of the components of the metal coordination complex.

Antimetabolites interfere with DNA production and thus cell division and the growth of tumors. Antimetabolites, which are analogs of nucleosides, disrupt incorporation of the natural building blocks of DNA, either by direct competition or by inhibition of DNA production through inhibition of dihydrofolate reductase. Many of these antimetabolites belong to a class of compound called purines. The purine analogs include azathioprene, mercaptopurine, thioguanine, fludarabine, arabinofuranosylcytosine (ara-C), gemcitabine, pentostatin and cladribine.

It has been shown that incorporation of fludarabine into leukemic cell DNA appears to be required for lethality. Furthermore, HDACi markedly increases fludarabine induced mitochondrial injury and apoptosis in a sequence-dependant manner, resulting in highly synergistic antileukemic interactions. Moreover, the enhanced lethality of the drug combination is associated with perturbations in several signal transduction pathways such as ERK inactivation, JNK activation, expression of apoptotic proteins and increases in ROS. (S. C. Maggio et al., The Histone Deacetylase Inhibitor MS-275 Interacts Synergistically with Fludarabine to Induce Apoptosis in Human Leukemia Cells, Cancer Res., 2004, 64 (7), 2590-600).

Prior exposure of leukemic cells to HDACi maximizes fludarabine lethality, indicating that HDAC inhibitors trigger time-dependant events that increase the apoptotic potency of fludarabine. Other studies have shown that ROS increase, mitochondrial dysfunction, caspase activation and loss of clonogenic survival all contribute to this synergistic potentiation.

Thus it is an embodiment of this invention that purine analogs that act as DNA antimetabolites when combined with an HDAC inhibitor in a synergistic manner will potentiate each other in promoting cell death in leukemic cells. It is a further embodiment of this invention that the synergy between the purine analog and the HDACi is optimized by precise kinetic control imparted through metal coordination of both the purine analog and the HDACi. In a preferred embodiment of the invention, the purine analog and the HDACi will form stable metal complexes. Mercaptopurine can form stable metal complexes, therefore in a preferred embodiment of the invention the purine analog is mercaptopurine. Likewise, SAHA can form stable metal complexes, therefore in another preferred embodiment of the invention the HDACi is SAHA. In a most preferred embodiment of the invention the antileukemia drug is a mercaptopurine:metal:SAHA coordination complex.

Lung Cancer

Alimta is an antimetholite with a molecular structure similar to folic acid. Its indications are for the treatment of pleural mesothelioma and non-small lung cell cancer. Folic acid and vitamin B-12 help manage Alitma's toxicity. (C&E News, Apr. 16, 2007, p. 45). Thus, a combination of alimta and folic acid synergistically delivered as described herein will potentiate the effects of alimta by reducing its toxicity. Therefore, Alimta-metal-folic acid and Alimta-metal-vitamin B-12 are embodiments of this invention.

Use in the Treatment of Cardiovascular Disorders

The importance of combination therapy to control blood pressure is well known and it has been estimated that 70% of patients with cardiovascular conditions will require combination therapy. (J. L. Pool, Direct Renin Inhibition: Focus on Aliskiren, J. Manag. Care Pharm., 2007, 13 (8 Suppl B), 21-33). Aliskiren, which is a direct renal inhibitor (DRI), is gaining importance in treating hypertension but has some adverse effects. These adverse effects may be avoided when used in combination with other cardiovascular drugs. Since renin is an upstream regulator of BP and angiotensin converting enzyme inhibitor (ACEI) and angiotensin II receptor antagonist (ARB) downstream, it makes sense that they would potentiate each other. Thus it is an embodiment of this invention that aliskiren be combined with an ACEI or an ARB in a metal complex having beneficial effects in treating hypertension and other related disease states. Most recently, the positive benefits of combining aliskiren and the ARB, losartan, to treat type 2 diabetic patients with diabetic nephropathy and hypertension due to the synergistic effects of dual blockade of the renin-angiotensin-aldosterone system (RAAS) has been reported. (S. Anderson & R. Komers, Aliskiren Combined With losartan in Diabetes and Nephropathy, N. Engl. J. Med., 2008, 359 (10), 1069; author reply 1069-70).

Combining agents that increase plasma renin activity (PRA) with agents that neutralize this activity appears to be a rational approach to treating hypertension. This duo effect from PRA highlights the importance of diuretics in balancing this effect. Moreover, combination therapy reduces the incidence of hypokalemia. (Tekturna, http://www.medscape-.com/infosite/tekturna/article-pharmocology). Thus it is an embodiment of this invention that aliskiren be combined with a diuretic in a metal complex and that the new metal coordination complex have optimum potentiated effects in treating hypertension and other related disease states. It stands to reason that diuretics can also be combined in a metal coordination complex with ARB's and ACEI's to potentiate the antihypertensive effects of those biologically active agents and thus ACEI-Mg-furosemide, ARB-Mg-furosemide and aliskiren-Mg-furosemide are preferred embodiments of this invention.

Ranolazine is a novel partial inhibitor of fatty acid oxidation and selective inhibitor of late sodium channels in myocardial cells which appears to ameliorate symptoms of angina due to myocardial ischemia without adversely altering cardiac hemodynamics. Ranolazine shifts adenosine-5'-triphosphate production from ischemia-induced fatty acid production to more oxygen-efficient carbohydrate oxidation and decreases associated myocardial sodium influx thereby reducing cellular calcium overload, which decreases left ventricular wall tension and further reduces myocardial oxygen demand.

Ranolazine is indicated for treatment of chronic stable angina in individuals with angina refractory to more standard anti-anginal medications. It has been shown to decrease angina episodes in individuals with coronary artery disease on maximal doses of amlodipine. In addition, it has been shown to both decrease angina episodes and increase exercise tolerance in individuals taking concomitant atenolol, amlodipine or diltiazem without significantly altering either the heart rate or blood pressure. Ranolazine, along with other late sodium-channel blockers, may also be used in the treatment of congestive heart failure, myocardial infarctions, cardiac arrhythmias, diastolic dysfunction and intermittent claudication.

It is an embodiment of this invention that FMDD complex formulations of ranolazine combined with calcium-channel blockers such amlodipine, diltiazem and verapamil will synergistically reduce the influx of damaging calcium into ischemic myocardium in the medical settings listed above while improving cardiac contractility, increasing coronary blood flow and reducing myocardial oxygen demand. A preferred embodiment of this invention is Ranolazine-Mg-Diltiazem. Other embodiments of this invention which would synergistically exploit the known anti-ischemic properties of beta-blockers and nitrates would be Ranolazine-Mg-metoprolol and Ranolazine-Mg-isosorbide mononitrate. Additionally, Ranolazine-Mg-furosemide would be beneficial in patients with congestive heart failure due to decreased left ventricular function secondary to myocardial ischemia.

Use in the Treatment of Gastrointestinal Disorders

Crohn's disease (CD) and ulcerative colitis (UC) are chronic inflammatory diseases of the gastrointestinal tract encompassed by the term, inflammatory bowel diseases (IBD). Aminosalicylates such as mesalamine (5-aminosalicylic acid) have historically been a mainstay in the treatment of UC and CD, having multiple anti-inflammatory effects including inhibition of cyclooxygenase, lipoxygenase, B-cells and inflammatory cytokines. (R: B. Sartor, Mechanisms of Disease: Pathogenesis of Crohn's Disease and Ulcerative Colitis, Nat. Clin. Pract. Gastroenterol. Hepatol., 2006, 3 (7), 390-407). Additionally, mesalamine and its formulations have been shown to activate specific peroxisome proliferator-activator receptor ligand (PPAR), nuclear receptors that regulate cellular differentiation and induce apoptosis. (W. J. Sandborn, Oral 5-ASA Therapy in Ulcerative Colitis: What Are the Implications of the New Formulations?, J. Clin. Gastroenterol., 2008, 42 (4), 338-44).

Administration of systemic and non-systemic steroids in IBD result in a broad spectrum of ameliorating immunological effects including inhibition of migration of neutrophils to inflammatory sites, suppression of the recruitment and proliferation of lymphocytes, monocytes and macrophages, and reduced production of inflammatory mediators such as cytokines, leukotrienes and prostaglandins (Sandborn, Id.). In turn, immunomodulators such as 6-mercaptopurine (6-MP) and its prodrug azathioprine (AZA) interfere with nucleic acid synthesis, thus inhibiting the proliferation of activated lymphocytes and inducing apoptosis in patients with refractory or steroid-resistant disease.

Mycophenolate mofetil (MMF), a prodrug of mycophenolic acid, also interferes with purine metabolism by inhibiting synthesis of guanosine nucleotides such as GTP and thereby reducing the proliferation of T-cells. Secondary effects of MMF may be to induce tolerance of dendritic cells to antigenic stimuli, thus rendering T-cells less responsive and inhibition of adhesion molecule expression on lymphocytes via reduced glycosylation. MMF's mechanism of action is similar to azathioprine and is also considered for use in steroid-resistant and refractory IBD patients.

While the aminosalicylates remain the first-line therapy for the induction and maintenance of mild to moderate UC, their efficacy in the treatment of CD is less supported by the literature. Additionally, a proportion of IBD patients are refractory to aminosalicylates requiring chronic administration of various steroid preparations, especially in patients with CD. These steroid-dependent subgroups of patients typically require concurrent use of AZA and 6-MP as a steroid-sparing strategy, although these immunosuppressant agents may be associated with multiple adverse effects, especially in patients who lack thiopurine methyl transferase (TPMT), an enzyme which metabolizes azathioprine and rendering them at increased risk of bone marrow suppression and other toxicities Combinatorial therapies for IBD have the theoretical advantage of synergistic immunosuppression of cellular and humoral inflammation, reduction of drug toxicity in steroid-dependent or steroid-refractory patients, and improved patient compliance, which may reduce the risk of neoplastic transformation in chronic UC patients. For example, the FMDD complex combination of tixocortol, a high potency topical corticosteroid with good metabolic stability in the bowel, with mesalamine would have theoretical therapeutic benefits for both the induction and maintenance of UC and CD. This benefit may manifest by enhancing delivery of the active moieties to the targeted inflammation by reducing systemic absorption while reducing overall dosing requirements. This "steroid-sparing" effect of this FMDD entity would also result in improved patient compliance and reduced long-term toxicities. An FMDD complex combination of tixocortol and AZA/6-MP would demonstrate the same therapeutic benefits in early or steroid-dependent IBD patients.

The FMDD complex combination of MMF with AZA/6-MP may be useful in steroid-refractory IBD patients or to maintain remission in severe and progressive disease where surgical intervention is being contemplated as a last resort. Both drugs have a similar and possibly synergistic mechanism of action by interfering with purine synthesis and suppressing rapidly proliferating T-cell and B-cell lineages. Both drugs have independently demonstrated benefit in IBD who fail to show improvement to administration of systemic and parental corticosteroids in fulminant cases. Alternatively, FMDD complex combinations of MMF with tixocortol and mesalamine may be beneficial in IBD patients who have shown toxicity or resistance to AZA/6-MP administration or have reduced or absent TPMT enzyme activity.

Metal chelation of FMDD complexes containing mesalamine may enhance the distal delivery of the active drug moieties, such as typically seen with the bacterial azoreductase cleavage of IBD patients treated with sulfasalazine, by mimicking the azo-bond which prevents the premature intestinal absorption and hepatic metabolism of mesalamine. This effect, in turn, would further reduce the incidence of toxicity and poor patient compliance caused by the unintended systemic absorption of mesalamine.

Use in the Treatment of Diabetes

It has been shown that insulin's action in facilitating the metabolism of glucose is potentiated by the co-administration of certain glycan containing insulin mediators. Of particular note is the glycemic control imparted by the aminosugar-inositol disaccharides. It is especially noteworthy that D-chiroinositol (DCI), either as part of a disaccharide or alone has glycemic modulation effects in vivo. (J. Larner et al., Isolation, Structure, Synthesis, and Bioactivity of a Novel Putative Insulin Mediator, A Galactosamine Chiro-inositol Pseudodisaccharide Mn2+ Chelate With Insulin-like Activity, J. Med. Chem., 2003, 46 (15), 3283-91). Therefore, the insulin-metal-inositol coordination complex is an embodiment of this invention. Since insulin is commercially available as a zinc complex, it is a preferred embodiment of this invention that the diabetes therapeutic agent is insulin-zinc-inositol. In an even more preferred embodiment of the invention, the complex is insulin-zinc-DCI. In a most preferred embodiment of the invention the complex is insulin-zinc-2-deoxy-2-amino-galactopyranosyl-DCI.

Diabetes provides a unique application for FMDD because if the metal vanadium were used, an additional therapeutic effect could be imparted beyond what the two biologically active ligands (e.g. inositol and insulin) provide. Thus, it is an additional embodiment of this invention that the metal is vanadium.

Other FMDD Ligands

The number and types of FMDD ligands and FMDD complexes and diseases and medical conditions treated by FMDD complexes are not intended to be limited by the disclosure herein. Other complexes and medical conditions may be recognized by those of skill in the art upon contemplation of the present disclosure.

For example there are biologically active agents with known benefits for various neurodegenerative/neurological conditions. In addition to the already mentioned methylfolate and carnosine, 1) gamma-3-fatty acids, which have been used to treat schizophrenia and ADHD, 2) cannabinoids, which have been used in the treatment of pain, coeliac disease, Alzheimer's disease, multiple sclerosis and epilepsy, 3) flupirtine, an NMDAR antagonist, which has been used in the treatment of pain, Parkinson's disease and fibromyalgia, 4)

glutathione, a tripeptide which plays a major role as an antioxidant and co-factor in numerous cellular metabolisms, and has been used in the treatment of PD, Autism, and male infertility, 5) curcumin, a beta-diketone which has been used to treat gliomas and other cancers, and is also an inhibitor of hepatic P-glycoprotein which may result in beneficial chemosensitization, and 6) N-acetylcysteine, which has been used to treat Autism, are all viable FMDD candidates that can potentiate the effects of other pharmaceutically active agents. (Yoshikawa et al., Inflamatory Bowel Disease Preventative and Curative Agent Containing Zinc L-carnosine Salt as Active Ingredient, 1991, 1993; T. Yoneta et al., Wound Healing Accelerators, 1997; Atkins, Specialty Pharma., May 2005, 1 (1), p. 31).

Moreover, (−)-Epigallocatechin-3-gallate alters cleavage of amyloid precursor protein decreasing production of amyloid plaques, thus making that agent an FMDD ligand candidate for the treatment of Alzheimer's disease. (J. Tan, Neurosci., 2005, 25, 8807).

It is an embodiment of this invention that the combination of FMDD ligands, metal, and other ingredients or components imparts thermodynamic stability to the entire metal coordination complex. It is an embodiment of this invention, that FMDD ligands that are designed to provide thermodynamic stability to the metal coordination complex, such as salicylaldehyde, dipyridyl or ethylenediamine, are incorporated into the drug:metal complexes to impart beneficial physicochemical properties. It is a further embodiment of this invention that the benefit of the FMDD ligand is to stabilize the drug:metal complex in certain environments, such as in biological systems.

In a preferred embodiment of the invention the disease state whose treatment is potentiated by this invention includes pain, cancer, Parkinson's disease, epilepsy, ADHD, Alzheimer's disease, hypertension, schizophrenia, multiple sclerosis, migraine headaches and coeliac disease. In a more preferred embodiment of the invention the disease state whose treatment is potentiated by this invention is Parkinson's disease. In a most preferred embodiment of this invention the disease state whose treatment is potentiated by this invention is pain management.

According to the present disclosure, one embodiment may include a coordination complex including a first biologically active moiety, a second biologically active moiety, and a metal, wherein the first biologically active moiety and second biologically active moiety are bound to the metal by covalent coordination bonds, and wherein the first biologically active moiety and second biologically active moiety are different. In certain embodiments, the first biologically active moiety and the second biologically active moiety are capable of potentiating each other.

Certain embodiments may include a coordination complex, wherein the first biologically active moiety and the second biologically active moiety are selected from the group consisting of opioids, NMDA receptor antagonists, voltage-gated ion channel blockers, NSAIDs, acetylcholine receptor agonists, adenosine neurotransmitters, P2 receptor antagonists, cannabinoids, vanilloids, VR1 receptor agonists, substance P, NK receptor antagonists, CGRP1-receptor antagonists and nitric oxide.

Certain other embodiments may include a coordination complex, wherein the first biologically active moiety and the second biologically active moiety are selected from the group consisting of triptans, NSAIDs, and opioids, modulators of voltage-gated sodium and calcium channels, GABA receptors and the AMPA/kainate subtype glutamate receptors, GABA uptake inhibitors, voltage-dependant sodium channels blockers, glutamate-mediated exicitatory neurotransmission reducers, excess nitric oxide production inhibitors, hydroxyl radical scavengers, carbonic anhydrase inhibitors, antioxidants, norepinephrine release inhibitors, 5-HT2 receptor modulators, adenosine neurotransmitters, vanilloids and the VR1 receptor agonists, Substance P, CGRP1-receptor and NK receptor antagonists.

Further embodiments may include a coordination complex, wherein the first biologically active moiety and the second biologically active moiety are selected from the group consisting of ionotropic glutamate receptor antagonists and agonists, metabotropic glutamate receptor antagonists, MAO-B inhibitors, dopamine receptor agonists, and NMDA receptor antagonists.

Still further embodiments may include a coordination complex, wherein the first biologically active moiety and the second biologically active moiety are selected from the group consisting of NMDA receptor antagonists, HDAC inhibitors, cannabinoids, folic acid derivatives and carnosine-related compounds. As used herein, "carnosine-related compounds" include carnosine, anserine, and homocarnosine.

Certain embodiments may include a coordination complex, wherein the first biologically active moiety and the second biologically active moiety are selected from the group consisting of NMDA receptor antagonists, polyamine site antagonists, glycine-β receptor antagonists, carnosine-related compounds, and cannabinoids.

Other embodiments may include a coordination complex, wherein the first biologically active moiety and the second biologically active moiety are selected from the group consisting of statins, immunosuppressants, steroids, AMPK activators, anti-inflammatory reagents and cannabinoids.

Still other embodiments may include a coordination complex, wherein the first biologically active moiety and the second biologically active moiety are selected from the group consisting of anti-psychotics, gamma-3-fatty acids, and glutamic acid analogs.

Further embodiments may include a coordination complex, wherein the first biologically active moiety and the second biologically active moiety are selected from the group consisting of AMPA receptor agonists, AMPA receptor antagonists, NMDA receptor antagonists, carnosine-related compounds, gamma-3-fatty acids, G-protein receptor antagonists, antioxidants, anti-inflammatory reagents, glycine-site NMDA agonists, GABA receptor agonists and metabotropic glutamate receptor antagonists.

Further still, certain embodiments may include a coordination complex, wherein the first biologically active moiety and the second biologically active moiety are selected from the group consisting of antiangiogenesis agents, cytotoxic agents, antiandrogens, GnRH agonist, HDAC inhibitors, topoisomerase II inhibitors, antimetabolites, tumor necrosis factor-related apoptosis ligands (TRAIL), retinoic acid derivatives and vitamins.

Certain embodiments may include a coordination complex, wherein the first biologically active moiety and the second biologically active moiety are selected from the group consisting of direct renal inhibitors, angiotensin converting enzyme inhibitors, angiotensin II receptor antagonists, late sodium-channel blockers, calcium-channel blockers, and partial inhibitors of fatty acid oxidation.

Other embodiments may include a coordination complex, wherein the first biologically active moiety and the second biologically active moiety are selected from the group consisting of aminosalicylates, steroids, immunomodulators, cannabinoids, PPAR ligand activators, anti-inflammatory reagents and P-glycoprotein inhibitor.

Still other embodiments may include a coordination complex, wherein the first biologically active moiety and the second biologically active moiety are selected from the group consisting of glycan containing insulin mediators, sulfonylureas, biguanides, thiazolidinediones, PPAR ligand activators and inositols.

Certain embodiments according to the present disclosure include a method of treating a condition, including administering to a patient in need thereof a coordination complex comprising a first biologically active moiety, a second biologically active moiety, and a metal, wherein the first biologically active moiety and the second biologically active moiety are bound to the metal by covalent coordination bonds, and wherein the first biologically active moiety and the second biologically active moiety are different. In some embodiments, the condition may include pain, migraines, Parkinson's disease, Alzheimer's disease, multiple sclerosis, schizophrenia, attention deficit hyperactive disorder, autism spectrum disorders, cancer, hypertension, digestive diseases, diabetes, epilepsy, and combinations of any thereof.

In certain embodiments, the ligands may bind to the metal, and form a ring structure. In other embodiments, the ring structure is selected from the group consisting of a four member ring, a five member ring, a six member ring, a seven member ring, and an eight member ring. In further embodiments, the ring structure is selected from the group consisting of a five member ring and a six member ring.

Any suitable route of administration may be employed for providing a mammal, especially a human with an effective dosage of a compound of the present invention. For example, oral, rectal, topical, parenteral, ocular, pulmonary, nasal, and the like may be employed. Treatment of animals, especially a human, with an effective dosage of an embodiment of the present disclosure would involve the administration of the compound or composition in an appropriate form to the animal. The embodiments of the present disclosure can be administered in a variety of ways including but not limited to oral, parenteral, nasal, buccal, rectal, vaginal, ocular, pulmonary or topical. Alternatively, administration may be by intratracheal instillation, bronchial instillation, intradermal, subcutaneous, intramuscular, intraperitoneal or intravenous injection. Dosage forms include tablets, troches, dispersions, suspensions, solutions, capsules, creams, ointments, aerosols, and the like. They may be conveniently presented in unit dosage form and prepared by any of the methods well-known in the art of pharmacy.

The following examples are intended to illustrate, but not to limit, the scope of the invention. It is to be understood that other procedures known to those skilled in the art may alternatively be used.

EXAMPLES

Based on the methodology currently employed by the present inventors to prepare metal coordinated and heteroligated pharmaceuticals, the chemistry adapts well to parallel synthesis and purification instrumentation. The Syncore Polyvap/Reactor (Buchi Syncore Reactor R24, includes the vacuum/inert gas cover, reflux module, and the standard rack R24, BÜCHI Labortechnik AG, Switzerland) gives high efficiency and maximum flexibility for parallel and combinatorial synthesis. Work-up and purification is achieved utilizing Oasis HLB (hydrophilic-lipophilic reversed-phase solid-phase extraction) cartridges (Waters Corporation, Milford, Mass.) employing a vacuum extraction manifold capable of processing multiple samples. Two cases: 1) Dopa HLP's are currently prepared by adding DOPA, an amino acid, and solvent, followed by $Ba(OH)_2$ to a flask under an inert atmosphere with stirring. Metal sulfate is then added and the reaction is heated, filtered to remove $BaSO_4$, and loaded onto a solid phase extraction cartridge. The unreacted amino acids elute in the aqueous fraction, the (dopa)metallo(amino acid) in 20% MeOH, and any remaining $BaSO_4$ is retained. 2) (salicylato)zinc(amino acid) is currently prepared by reacting $Zn(sal)_2$ with an amino acid in $H_2O$ with heat. The reaction is filtered and loaded on to a solid phase extraction cartridge and eluted with 40% MeOH/$H_2O$. These are simple procedures involving unit operations of mixing, de-gassing, heating, filtration, and solid-phase extraction.

Example 1

(DOPA)Calcium(Carnosine)

Figure 14:
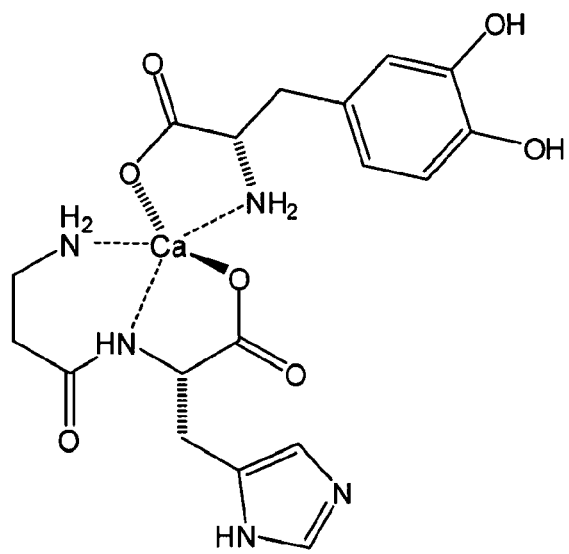
FIG. 14 shows the chemical structure for (DOPA)calcium (carnosine)

FIG. 14 depicts an embodiment including (DOPA)calcium (carnosine). To a 2-neck 100 mL round bottom flask equipped with a magnetic stirrer and $N_2$ inlet were added L-DOPA (250.0 mg, 1.27 mmol) and carnosine (286.5 mg, 1.27 mmol). Water (50 mL) was added and the mixture heated until the solids dissolved. Calcium methoxide (129.5 mg, 1.27 mmol) was added in one portion. The orange solution was stirred for 1 hour at room temperature. Solvent was removed under reduced pressure leaving a dark brown solid. $^1$H NMR ($D_2O$) δ 7.66 (s; 1H), 6.93 (s; 1H), 6.74 (d; J=7.8 Hz; 1H), 6.66 (d; J=2.2 Hz; 1H), 6.54 (dd; J=7.8 Hz, 2.2 Hz; 1H), 4.47 (dd; J=9.2 Hz, 4.6 Hz; 1H), 3.70 (dd; J=7.8 Hz, 5.2 Hz; 1H), 3.13 (dd; J=15.2 Hz, 4.6 Hz; 1H), 3.04-2.99 (m; 3H) 2.95 (dd; J=15.2 Hz, 9.2 Hz; 1H), 2.81 (dd; J=14.0 Hz, 7.8 Hz; 1H), 2.57-2.48 (m; 2H).

Carnosine $^1$HMR ($D_2O$) δ 7.71 (s; 1H), 6.95 (s; 1H), 4.47 (dd; J=8.8 Hz, 4.8 Hz; 1H), 3.22 (t; J=6.8 Hz; 2H), 3.13 (dd; J=15.2 Hz, 4.8 Hz; 1H), 2.97 (dd; J=15.2 Hz, 8.8 Hz; 1H), 2.68-2.63 (m; 2H).

Example 2

(DOPA)Magnesium(Carnosine)—Method 1

Figure 15:
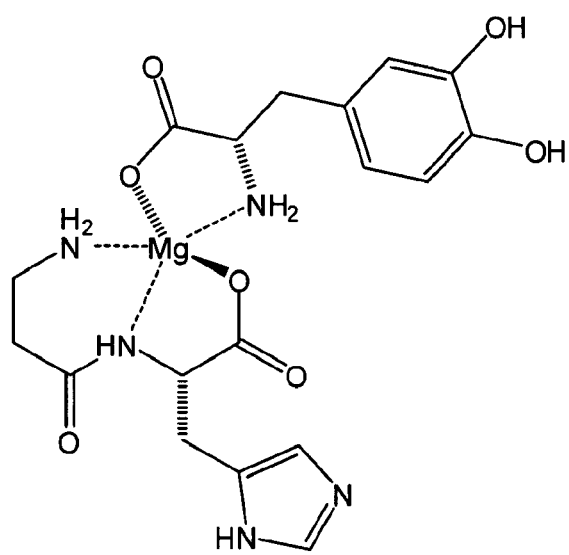
FIG. 15 shows the chemical structure for (DOPA)magnesium(carnosine)

FIG. 15 depicts an embodiment of the present disclosure including (DOPA)magnesium(carnosine). To a 2-neck 100 mL round bottom flask equipped with a magnetic stirrer and $N_2$ inlet were added L-DOPA (218 mg, 1.11 mmol) and carnosine (250 mg, 1.11 mmol). Water (50 mL) was added and the mixture heated until the solids dissolved. Magnesium t-butoxide (202 mg, 1.11 mmol) was added in one portion. The orange solution was stirred for 1 hour at room temperature. Solvent was removed under reduced pressure leaving a dark brown solid. $^1$H NMR ($D_2O$) δ 7.67 (s; 1H), 6.93 (s; 1H), 6.58 (br d; J=6.4 Hz; 1H), 6.51 (br s; 1H), 6.42 (br d; J=6.4 Hz; 1H), 4.46 (dd; J=9.0 Hz, 4.6 Hz; 1H), 3.78 (dd; J=8.4 Hz, 4.8 Hz; 1H), 3.15-3.03 (m; 4H), 2.95 (dd; J=15.2 Hz, 9.0 Hz; 1H), 2.81 (dd; J=14.4 Hz, 8.4 Hz; 1H), 2.58-2.54 (m; 2H).

Example 3

(DOPA)Magnesium(Carnosine)—Method 2

FIG. 15 depicts an embodiment of the present disclosure including (DOPA)magnesium(carnosine). To a 50 mL round bottom flask equipped with a magnetic stirrer and $N_2$ inlet was added carnosine (100 mg, 0.442 mmol). DMF (20 mL) was added to form a suspension. Magnesium t-butoxide (80.4 mg, 0.442 mmol) was added in one portion. The suspension was stirred for 24 hours at room temperature. To the reaction L-DOPA (87.1 mg, 0.442 mmol) was added in one portion. The suspension was stirred 24 hours. Solvent was removed under reduced pressure leaving a pale yellow solid. Purification was by SPE. $^1$H NMR (D$_2$O) δ 7.66 (s; 1H), 6.93 (s; 1H), 6.54 (br d; J=6.8 Hz; 1H), 6.47 (br s; 1H), 6.39 (br d; J=6.8 Hz; 1H), 4.46 (dd; J=8.8 Hz, 4.6 Hz; 1H), 3.75 (dd; J=8.4 Hz, 4.8 Hz; 1H), 3.13 (dd; J=15.2 Hz, 4.6 Hz; 1H), 3.06-3.01 (m; 3H), 2.95 (dd; J=15.2 Hz, 8.8 Hz; 1H), 2.79 (dd; J=14.4 Hz, 8.4 Hz), 2.56-2.52 (m; 2H). Metals analysis: 5.9% Mg (theoretical 5.4%).

Example 4

(SAHA)Magnesium(Mercaptopurine)

Figure 16:
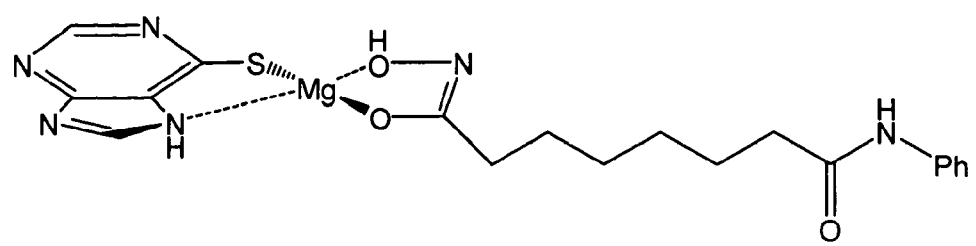
FIG. 16 shows the chemical structure of (SAHA)magnesium(mercaptopurine)

FIG. 16 depicts an embodiment of the present disclosure including (SAHA)magnesium(mercaptopurine). To a 25 mL round bottom flask equipped with magnetic stirrer, heating mantle, and reflux condenser were added mercaptopurine (57.8 mg, 0.378 mmol) and SAHA (100 mg, 0.378 mmol). Anhydrous methanol (10 mL) was added via syringe and the solids mostly dissolved. Magnesium acetate (81.1 mg, 0.378 mmole) was added and the suspension was refluxed for 16 hrs; all solids dissolved with heat. A small amount of precipitate formed after cooling. The reaction was vacuum filtered and solvent removed under reduced pressure yielding off white solid (170 mg, 0.387 mmole, 102%). $^1$H NMR (DMSO-d$_6$) δ 9.87 (s; 1H), 8.30 (s; 1H), 8.20 (s; 1H), 7.58 (d; J=7.6 Hz; 2H), 7.61-7.23 (m; 2H), 7.00 (t; J=7.4 Hz; 1H), 2.28 (t; J=7.2 Hz; 2H), 2.03-1.93 (m; 2H), 1.62-1.52 (m; 2H), 1.52-1.43 (m; 2H), 1.27 (br s; 3H). $^{13}$C NMR (DMSO-d$_6$) δ 171.7 (S8), 171.6 (M6), 169.5 (v. br. S1), 151.2 (M4), 145.4 (M2/M8), 145.3 (M8/M2), 139.7 (S10), 129.3 (M5), 129.0 (S11), 123.3 (S12), 119.5 (S13), 36.8 (S7), 31.9 (v. br. S2), 28.8 (S6), 28.6 (S3), 25.5 (S4/S5), 25.4 (S5/S4). Note: The $^{13}$C NMR (DMSO-d$_6$) chemical shift for the carbonyl carbons of SAHA are 171.7 and 169.5 ppm. The $^1$H NMR chemical shifts for uncoordinated mercaptopurine protons are 8.39 ppm and 8.19 ppm.

Example 5

(SAHA)Magnesium(Remacemide)

Figure 17:
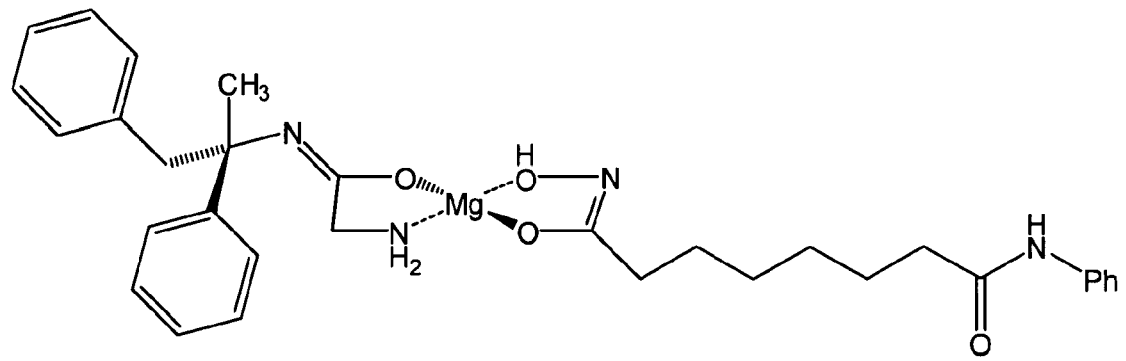
FIG. 17 shows the chemical structure of (SAHA)magnesium(remacemide)

FIG. 17 depicts an embodiment of the present disclosure including (SAHA)magnesium(remacemide). To a 25 mL round bottom flask equipped with magnetic stirrer, heating mantle, and reflux condenser were added SAHA (50 mg, 0.189 mmol) and remacemide (50.8 mg, 0.189 mmol). Anhydrous methanol (10 mL) was added via syringe and the solids dissolved. Magnesium acetate (40.6 mg, 0.189 mmole) was added and immediately dissolved. The solution was refluxed for 16 hrs. Solvent was removed from the clear solution under reduced pressure yielding a colorless solid. $^1$H NMR (CD$_3$OD) δ 7.54 (br dd; J=9.2 Hz, 0.8 (av) Hz; 1H), 7.34-7.24 (m; 3H), 7.23-7.16 (m; 2H); 7.06 (br t; J=7.4 Hz; 1H), 6.97-6.92 (m; 1H), 3.55-3.44 (m; 1H); 3.22-3.17 (m; 1H), 2.35 (t; J=7.6 Hz; 1H), 2.10 (t; J=7.6 Hz; 1H), 1.90 (s; 3H); 1.75-1.57 (m; 2H), 1.55 (s; 1H), 1.45-1.30 (m; 2H). $^{13}$C NMR (CD$_3$OD-d$_6$) δ 178.7, 173.1, 145.6, 138.5, 136.6, 130.5, 128.3, 127.7, 127.4, 126.2, 126.1, 125.2, 123.7, 119.8, 58.8, 45.0, 42.0, 36.4, 31.5, 28.5, 28.4, 25.4, 25.3, 22.7. Note: The $^{13}$C NMR (CD$_3$OD) chemical shifts for the carbonyl carbons of SAHA are 173.2 and 171.5 ppm.

Although the present invention has been described in terms of specific embodiments, changes and modifications can be made without departing from the scope of the invention which is intended to be defined only by the scope of the claims. All references cited herein are hereby incorporated by reference in their entirety, including any references cited therein.

What is claimed:

1. A coordination complex, comprising:
    a first biologically active moiety selected from gamma-3-fatty acids, cannabinoids, flupirtine, gluatathione, curcumin, N-acetylcysteine, p-glycoprotein inhibitors, (−)-epigallocatechin-3-gallate, anserine, and homocarnosine;
    a second biologically active moiety; and
    a non-platinum metal;
    wherein the first and second biologically active moieties are each bound to the metal by at least one binding site;
    wherein the first biologically active moiety and second biologically active moiety are different;
    wherein the first biologically active moiety and the second biologically active moiety both have a pharmacological effect on a target tissue.

2. The coordination complex of claim 1, further comprising a ligand.

3. The coordination complex of claim 2, wherein the ligand is selected from salicylaldehyde, dipyridyl, and ethylenediamine.

4. The coordination complex of claim 1, wherein the metal is selected from the group consisting of magnesium, calcium, iron, cobalt, nickel, copper, zinc, palladium, ruthenium, rhodium, aluminum, cadmium, vanadium, chromium, strontium, and tin.

5. The coordination complex of claim 1, further comprising a component selected from the group consisting of an amino acid, a lipid, a carbohydrate, a nucleic acid, and a peptide.

6. A method for enhancing the treatment of a disease, comprising:
    forming a coordination complex comprising a first biologically active moiety selected from selected from gamma-3-fatty acids, cannabinoids, flupirtine, glutathione, curcumin, N-acetylcysteine, p-glycoprotein inhibitors, (−)-epigallocatechin-3-gallate, anserine, and homocarnosine; a second biologically active moiety, and a non-platinum metal;
    wherein the first biologically active moiety and the second biologically active moiety are each bound to the metal by at least one binding site;
    wherein the first biologically active moiety and the second biologically active moiety are different.

7. The method of claim 6, wherein the coordination complex formed includes a ligand.

8. The method of claim 7, wherein the ligand is selected from salicylaldehyde, dipyridyl, and ethylenediamine.

9. The method of claim 6, wherein the metal is selected from the group consisting of magnesium, calcium, iron, cobalt, nickel, copper, zinc, palladium, ruthenium, rhodium, aluminum, cadmium, vanadium, chromium, strontium, and tin.

10. The method of claim 6, further comprising a component selected from the group consisting of an amino acid, a lipid, a carbohydrate, a nucleic acid, and a peptide.

11. A method of treating a disease, comprising:
    administering a coordination complex comprising a first biologically active moiety selected from selected from gamma-3-fatty acids, cannabinoids, flupirtine, glutathione, curcumin, N-acetylcysteine, p-glycoprotein inhibitors, (−)-epigallocatechin-3-gallate, anserine, and homocarnosine; a second biologically active moiety, and a non-platinum metal to a patient having a disease;

wherein the first and second biologically active moieties treat a disease by interacting with one or more tissues associated with the disease.

12. The method of claim 11, wherein the coordination complex formed includes a ligand.

13. The method of claim 12, wherein the ligand is selected from salicylaldehyde, dipyridyl, and ethylenediamine.

14. The method of claim 11, wherein the metal is selected from the group consisting of magnesium, calcium, iron, cobalt, nickel, copper, zinc, palladium, ruthenium, rhodium, aluminum, cadmium, vanadium, chromium, strontium, and tin.

15. The method of claim 11, further comprising a component selected from the group consisting of an amino acid, a lipid, a carbohydrate, a nucleic acid, and a peptide.

* * * * *